US007445922B2

(12) United States Patent
Nakane et al.

(10) Patent No.: US 7,445,922 B2
(45) Date of Patent: *Nov. 4, 2008

(54) ZYGOMYCETES-DERIVED ENDOGLUCANASE ENZYME LACKING CELLULOSE-BINDING DOMAIN

(75) Inventors: Akitaka Nakane, Saitama (JP); Yuko Baba, Saitama (JP); Jinichiro Koga, Saitama (JP); Hidetoshi Kubota, Saitama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 375 days.

This patent is subject to a terminal disclaimer.

(21) Appl. No.: 10/432,290

(22) PCT Filed: Nov. 21, 2001

(86) PCT No.: PCT/JP01/10188

§ 371 (c)(1),
(2), (4) Date: May 20, 2003

(87) PCT Pub. No.: WO02/42474

PCT Pub. Date: May 30, 2002

(65) Prior Publication Data

US 2004/0043400 A1    Mar. 4, 2004

(30) Foreign Application Priority Data

Nov. 21, 2000    (JP)    ............... 2000-354296

(51) Int. Cl.
```
C12N 9/26      (2006.01)
C12N 1/15      (2006.01)
C12N 1/21      (2006.01)
C12N 5/10      (2006.01)
C12N 15/00     (2006.01)
C12Q 1/34      (2006.01)
C12P 21/00     (2006.01)
C07K 14/00     (2006.01)
C07H 21/00     (2006.01)
C11D 3/386     (2006.01)
A61K 38/47     (2006.01)
```
(52) U.S. Cl. .............. 435/201; 435/18; 435/320.1; 435/69.1; 435/254.11; 435/252.3; 435/325; 510/300; 530/350; 536/23.1; 536/23.2; 424/94.61

(58) Field of Classification Search .............. 435/4, 435/6, 69.1, 183, 200, 252.3, 320.1, 210, 435/201, 18, 325, 254.11; 536/23.2, 23.4, 536/23.7, 23.74, 23.5, 23.1; 530/350; 510/114, 510/392, 515, 300

See application file for complete search history.

(56) References Cited

U.S. PATENT DOCUMENTS 6,921,655 B1 * 7/2005 Nakamura et al. .......... 435/200

FOREIGN PATENT DOCUMENTS

| EP | 1291431 A1 | 3/2003 |
| WO | WO 94/21801 A2 | 9/1994 |
| WO | WO 00/24879 A1 | 4/2000 |

OTHER PUBLICATIONS

Nguyen et al. Canadian J. Botany, 1984, vol. 62:2670-2676.*
Kvesitadze et al., European Congress of Biotechnol., 1984, 3 Meet, vol. 3, p. 23.*
Hornwer et al. (Sciences Des Aliments, 1987, vol. 8(2):361-380).*
Nguyen The et al. (Canadian J. Botany, 1984, vol. 62(12):2670-2676).*
Gilbert et al. (Mol. Microbiol., 1990, vol. 4:759-767), accession No. S68153, 1998.*
Mernitz et al. (Curr. Genet., 1996, vol. 29:490-495), accession No. S10521.*
Nakamura et al. (Gen Bank Accession No. AAB09821, Sep. 29, 2000).*
Gilkes et al. JBC, 1988, vol. 263(21):10401-7.*
Nakamura et al. GenBank Accession No. AAB09821, Sep. 25, 2000.*
Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Azevedo, H. et al., "Effects of agitation level on the absorption, desorption, and activities on cotton fabrics of full-length and core domains of EGV (*Humicola insolens*) and CenA (*Cellulomonas fimi*).", in Enzyme Microb. Technol., Aug. 2000, vol. 27, No. 3-5, pp. 325 to 329.
Takashima, S. et al., in "Comparison of gene structures and enzymatic properties between two endoglucanases from *Humicola grisea*" in J. Biotechnology, 1999, vol. 67, pp. 85-97.
Takashima, et al., "Isolation of the Gene and Characterization of the Enzymatic Properties of a Major Exoglucanase of *Humicola grisea* Without a Cellulose-Binding Domain," in Journal of Biochemistry, Japanese Biochemical Society, Tokyo, Japan, vol. 124, No. 4, Oct. 1998, pp. 717-725.

* cited by examiner

*Primary Examiner*—Delia M Ramirez
(74) *Attorney, Agent, or Firm*—Posz Law Group, PLC

(57) ABSTRACT

This invention relates to a protein that is a *Zygomycetes*-derived endoglucanase lacking the cellulose-binding domain and exhibits endoglucanase activity, and a method for using the same. This invention can enhance effects of an endoglucanase enzyme on fabric treatment such as reduction of fuzzing, improvement in feel and appearance, color clarification, partial color change, and softening of cellulose-containing fabrics and on performance improvement in the deinking of waste paper and drainage of paper pulp.

24 Claims, No Drawings

ID NO: 1, 3, 5, 7, 9, or 11, wherein the cellulose-

SEQUENCE LISTING

```
<160> NUMBER OF SEQ ID NOS: 43

<210> SEQ ID NO 1
<211> LENGTH: 338
<212> TYPE: PRT
<213> ORGANISM: Rhizopus oryzae CP96001
<220> FEATURE:
<221> NAME/KEY: sig_peptide
<222> LOCATION: (-23)...(-1)
<220> FEATURE:
<221> NAME/KEY: mat_peptide
<222> LOCATION: (1)...(315)

<400> SEQUENCE: 1

Met Lys Phe Ile Thr Ile Ala Ser Ser Ala Leu Leu Ala Leu Ala Leu
        -20                 -15                 -10
```

```
Gly Thr Glu Met Ala Ser Ala Ala Glu Cys Ser Lys Leu Tyr Gly Gln
        -5              1                   5
Cys Gly Gly Lys Asn Trp Asn Gly Pro Thr Cys Cys Glu Ser Gly Ser
 10              15                  20                  25
Thr Cys Lys Val Ser Asn Asp Tyr Tyr Ser Gln Cys Leu Pro Ser Gly
                 30                  35                  40
Ser Ser Gly Asn Lys Ser Ser Glu Ser Ala His Lys Lys Thr Thr Thr
             45                  50                  55
Ala Ala His Lys Lys Thr Thr Thr Ala Ala His Lys Lys Thr Thr Thr
             60                  65                  70
Ala Pro Ala Lys Lys Thr Thr Thr Val Ala Lys Ala Ser Thr Pro Ser
 75                  80                  85
Asn Ser Ser Ser Ser Ser Gly Lys Tyr Ser Ala Val Ser Gly Gly
 90                  95                 100                 105
Ala Ser Gly Asn Gly Val Thr Thr Arg Tyr Trp Asp Cys Cys Lys Ala
             110                 115                 120
Ser Cys Ser Trp Pro Gly Lys Ala Asn Val Ser Ser Pro Val Lys Ser
             125                 130                 135
Cys Asn Lys Asp Gly Val Thr Ala Leu Ser Asp Ser Asn Ala Gln Ser
         140                 145                 150
Gly Cys Asn Gly Gly Asn Ser Tyr Met Cys Asn Asp Gln Pro Trp
         155                 160                 165
Ala Val Asn Asp Asn Leu Ala Tyr Gly Phe Ala Ala Ala Ile Ser
170                 175                 180                 185
Gly Gly Gly Glu Ser Arg Trp Cys Cys Ser Cys Phe Glu Leu Thr Phe
             190                 195                 200
Thr Ser Thr Ser Val Ala Gly Lys Lys Met Val Val Gln Val Thr Asn
         205                 210                 215
Thr Gly Gly Asp Leu Gly Ser Ser Thr Gly Ala His Phe Asp Leu Gln
         220                 225                 230
Met Pro Gly Gly Gly Val Gly Ile Phe Asn Gly Cys Ser Ser Gln Trp
 235                 240                 245
Gly Ala Pro Asn Asp Gly Trp Gly Ser Arg Tyr Gly Gly Ile Ser Ser
250                 255                 260                 265
Ala Ser Asp Cys Ser Ser Leu Pro Ser Ala Leu Gln Ala Gly Cys Lys
             270                 275                 280
Trp Arg Phe Asn Trp Phe Lys Asn Ala Asp Asn Pro Ser Met Thr Tyr
             285                 290                 295
Lys Glu Val Thr Cys Pro Lys Glu Ile Thr Ala Lys Thr Gly Cys Ser
         300                 305                 310
Arg Lys
    315

<210> SEQ ID NO 2
<211> LENGTH: 1017
<212> TYPE: DNA
<213> ORGANISM: Rhizopus oryzae CP96001
<220> FEATURE:
<221> NAME/KEY: sig_peptide
<222> LOCATION: (1)...(69)
<220> FEATURE:
<221> NAME/KEY: mat_peptide
<222> LOCATION: (70)...(1017)

<400> SEQUENCE: 2 atg aag ttt att act att gcc tct tcc gct ctc ttg gct ctc gcc ctc        48
```

```
Met Lys Phe Ile Thr Ile Ala Ser Ser Ala Leu Leu Ala Leu Ala Leu
            -20                 -15                 -10 ggt act gaa atg gcc tct gct gct gaa tgt agc aaa ttg tat ggt caa      96
Gly Thr Glu Met Ala Ser Ala Ala Glu Cys Ser Lys Leu Tyr Gly Gln
         -5                   1                   5 tgt ggt ggt aag aac tgg aat ggc cct act tgt tgt gaa tct gga tcc     144
Cys Gly Gly Lys Asn Trp Asn Gly Pro Thr Cys Cys Glu Ser Gly Ser
 10                  15                  20                  25 acc tgt aaa gta agc aac gat tac tac tct caa tgt ctt ccc tct gga     192
Thr Cys Lys Val Ser Asn Asp Tyr Tyr Ser Gln Cys Leu Pro Ser Gly
                 30                  35                  40 agc agt ggc aat aaa tct tct gaa agt gct cac aag aag act acc act     240
Ser Ser Gly Asn Lys Ser Ser Glu Ser Ala His Lys Lys Thr Thr Thr
             45                  50                  55 gct gct cac aag aag act act acc gct gct cat aaa aag act acc act     288
Ala Ala His Lys Lys Thr Thr Thr Ala Ala His Lys Lys Thr Thr Thr
         60                  65                  70 gct cct gct aag aag act aca act gtt gcc aaa gct tcc acc cct tct     336
Ala Pro Ala Lys Lys Thr Thr Thr Val Ala Lys Ala Ser Thr Pro Ser
 75                  80                  85 aac tct agc tct agc tcc agc ggc aaa tat tcc gct gtc tct ggt ggt     384
Asn Ser Ser Ser Ser Ser Ser Gly Lys Tyr Ser Ala Val Ser Gly Gly
 90                  95                 100                 105 gcc tct ggt aac ggt gtc act act cgt tat tgg gat tgc tgt aag gcc     432
Ala Ser Gly Asn Gly Val Thr Thr Arg Tyr Trp Asp Cys Cys Lys Ala
                110                 115                 120 tcc tgt agc tgg ccc ggt aag gcc aat gtc agt tct cct gtc aag tcc     480
Ser Cys Ser Trp Pro Gly Lys Ala Asn Val Ser Ser Pro Val Lys Ser
            125                 130                 135 tgt aac aaa gat ggt gtc act gcc ctt agt gac agc aat gcc caa agt     528
Cys Asn Lys Asp Gly Val Thr Ala Leu Ser Asp Ser Asn Ala Gln Ser
        140                 145                 150 ggc tgt aac ggt ggt aac agt tac atg tgt aac gac aac caa cct tgg     576
Gly Cys Asn Gly Gly Asn Ser Tyr Met Cys Asn Asp Asn Gln Pro Trp
    155                 160                 165 gct gta aac gac aac ctt gcc tat ggt ttc gct gct gct gcc atc agt     624
Ala Val Asn Asp Asn Leu Ala Tyr Gly Phe Ala Ala Ala Ala Ile Ser
170                 175                 180                 185 ggt ggt ggt gaa tct cgc tgg tgc tgt tct tgt ttc gaa ctt act ttc     672
Gly Gly Gly Glu Ser Arg Trp Cys Cys Ser Cys Phe Glu Leu Thr Phe
                190                 195                 200 act tct acc tct gtt gct ggt aag aag atg gtt gtc caa gtc act aac     720
Thr Ser Thr Ser Val Ala Gly Lys Lys Met Val Val Gln Val Thr Asn
            205                 210                 215 act ggt ggt gat ctt ggc tcc tct act ggt gct cac ttt gac ttg caa     768
Thr Gly Gly Asp Leu Gly Ser Ser Thr Gly Ala His Phe Asp Leu Gln
        220                 225                 230 atg ccc ggt ggt ggt gtt ggt att ttc aat ggt tgt tcc agc caa tgg     816
Met Pro Gly Gly Gly Val Gly Ile Phe Asn Gly Cys Ser Ser Gln Trp
    235                 240                 245 ggt gct ccc aat gac ggt tgg ggc tca aga tac ggt ggt att tct tct     864
Gly Ala Pro Asn Asp Gly Trp Gly Ser Arg Tyr Gly Gly Ile Ser Ser
250                 255                 260                 265 gca tct gac tgc tct agt ctt cct tcc gca ctc caa gct ggt tgt aaa     912
Ala Ser Asp Cys Ser Ser Leu Pro Ser Ala Leu Gln Ala Gly Cys Lys
                270                 275                 280 tgg aga ttc aac tgg ttc aag aac gct gat aac cca agc atg act tac     960
Trp Arg Phe Asn Trp Phe Lys Asn Ala Asp Asn Pro Ser Met Thr Tyr
            285                 290                 295 aag gaa gtt acc tgt cct aag gaa atc acc gcc aag aca ggt tgt tca    1008
Lys Glu Val Thr Cys Pro Lys Glu Ile Thr Ala Lys Thr Gly Cys Ser
```

```
Lys Glu Val Thr Cys Pro Lys Glu Ile Thr Ala Lys Thr Gly Cys Ser
        300                 305                 310 aga aaa taa                                                                    1017
Arg Lys
    315

<210> SEQ ID NO 3
<211> LENGTH: 366
<212> TYPE: PRT
<213> ORGANISM: Rhizopus oryzae CP96001
<220> FEATURE:
<221> NAME/KEY: sig_peptide
<222> LOCATION: (-23)...(-1)
<220> FEATURE:
<221> NAME/KEY: mat_peptide
<222> LOCATION: (1)...(343)

<400> SEQUENCE: 3

Met Lys Phe Ile Thr Ile Thr Ser Ser Ala Leu Leu Ala Leu Ala Leu
            -20                 -15                 -10

Gly Thr Glu Met Ala Ser Ala Ala Lys Cys Ser Lys Leu Tyr Gly Gln
        -5                  1                   5

Cys Gly Gly Lys Asp Trp Asn Gly Pro Thr Cys Cys Glu Ser Gly Ser
10                  15                  20                  25

Thr Cys Lys Val Ser Asn Asp Tyr Tyr Ser Gln Cys Leu Ala Pro Glu
                30                  35                  40

Ser Asn Gly Asn Lys Ser Ser Glu Cys Ser Lys Leu Tyr Gly Gln Cys
                45                  50                  55

Gly Gly Lys Asp Trp Asn Gly Pro Thr Cys Cys Glu Ser Gly Ser Thr
            60                  65                  70

Cys Lys Val Ser Asn Asp Tyr Tyr Ser Gln Cys Leu Ala Pro Glu Ser
75                  80                  85

Asn Gly Asn Lys Thr Ser Glu Ser Ala His Lys Thr Thr Thr Thr Thr
90                  95                  100                 105

Ala Pro Ala Lys Glu Ile Thr Thr Thr Ala Lys Ala Ser Asn Ser Ser
            110                 115                 120

Asn Ser Ser Gly Lys Tyr Ser Ile Val Ser Gly Ala Ser Gly Asn
                125                 130                 135

Gly Val Thr Thr Arg Tyr Trp Asp Cys Cys Lys Ala Ser Cys Ser Trp
        140                 145                 150

Pro Gly Lys Ala Asn Val Ser Ser Pro Val Lys Ser Cys Asn Lys Asp
    155                 160                 165

Gly Val Thr Ala Leu Ser Asp Ser Asn Val Gln Ser Gly Cys Asn Gly
170                 175                 180                 185

Gly Asn Ser Tyr Met Cys Asn Asp Asn Gln Pro Trp Ala Val Asn Asp
                190                 195                 200

Asn Leu Ala Tyr Gly Phe Ala Ala Ala Ile Ser Gly Gly Gly Glu
            205                 210                 215

Ser Arg Trp Cys Cys Ser Cys Phe Glu Leu Thr Phe Thr Ser Thr Ser
        220                 225                 230

Val Ala Gly Lys Lys Met Val Ile Gln Val Thr Asn Thr Gly Gly Asp
    235                 240                 245

Leu Gly Ser Ser Thr Gly Ala His Phe Asp Leu Gln Met Pro Gly Gly
250                 255                 260                 265

Gly Val Gly Ile Phe Asn Gly Cys Ser Lys Gln Trp Gly Ala Pro Asn
                270                 275                 280

Asp Gly Trp Gly Ser Arg Tyr Gly Gly Ile Ser Ser Ala Ser Asp Cys
```

```
                      285                      290                      295
Ser Ser Leu Pro Ser Ala Leu Gln Ala Gly Cys Lys Trp Arg Phe Asn
            300                     305                     310

Trp Phe Lys Asn Ala Asp Asn Pro Ser Met Thr Tyr Lys Glu Val Thr
        315                     320                     325

Cys Pro Lys Glu Ile Thr Ala Lys Thr Gly Cys Ser Arg Lys
330                     335                     340

<210> SEQ ID NO 4
<211> LENGTH: 1101
<212> TYPE: DNA
<213> ORGANISM: Rhizopus oryzae CP96001
<220> FEATURE:
<221> NAME/KEY: sig_peptide
<222> LOCATION: (1)...(69)
<220> FEATURE:
<221> NAME/KEY: mat_peptide
<222> LOCATION: (70)...(1101)

<400> SEQUENCE: 4 atg aag ttt att act att acc tct tcc gct ctc ttg gct ctc gcc ctt         48
Met Lys Phe Ile Thr Ile Thr Ser Ser Ala Leu Leu Ala Leu Ala Leu
            -20                     -15                     -10 ggt act gaa atg gcc tct gct gct aaa tgt agc aag ctg tat ggt caa         96
Gly Thr Glu Met Ala Ser Ala Ala Lys Cys Ser Lys Leu Tyr Gly Gln
        -5                       1               5 tgt ggt ggt aag gac tgg aat ggc cct act tgt tgc gaa tct gga tcc        144
Cys Gly Gly Lys Asp Trp Asn Gly Pro Thr Cys Cys Glu Ser Gly Ser
10                  15                  20                  25 acc tgt aaa gta agc aac gat tac tac tct caa tgt ctt gcc cct gaa        192
Thr Cys Lys Val Ser Asn Asp Tyr Tyr Ser Gln Cys Leu Ala Pro Glu
                30                  35                  40 agc aac ggc aat aag tct tct gaa tgt agc aag ttg tat ggt caa tgt        240
Ser Asn Gly Asn Lys Ser Ser Glu Cys Ser Lys Leu Tyr Gly Gln Cys
            45                  50                  55 ggt ggt aag gac tgg aat ggc cct act tgt tgc gaa tct gga tcc acc        288
Gly Gly Lys Asp Trp Asn Gly Pro Thr Cys Cys Glu Ser Gly Ser Thr
        60                  65                  70 tgt aaa gta agc aac gat tac tac tct caa tgt ctt gcc cct gaa agc        336
Cys Lys Val Ser Asn Asp Tyr Tyr Ser Gln Cys Leu Ala Pro Glu Ser
75                  80                  85 aat ggc aat aaa act tct gaa agc gct cat aaa acg act act acc act        384
Asn Gly Asn Lys Thr Ser Glu Ser Ala His Lys Thr Thr Thr Thr Thr
90                  95                  100                 105 gct ccc gct aag gaa att aca act act gcc aaa gct tca aac tct tct        432
Ala Pro Ala Lys Glu Ile Thr Thr Thr Ala Lys Ala Ser Asn Ser Ser
                110                 115                 120 aac tct agc ggc aaa tac tcc att gtc tct ggt ggt gcc tct ggt aac        480
Asn Ser Ser Gly Lys Tyr Ser Ile Val Ser Gly Gly Ala Ser Gly Asn
            125                 130                 135 ggt gtc act act cgt tat tgg gat tgc tgt aag gcc tcc tgt agc tgg        528
Gly Val Thr Thr Arg Tyr Trp Asp Cys Cys Lys Ala Ser Cys Ser Trp
        140                 145                 150 ccc ggt aag gcc aat gtc agt tct cct gtc aag tcc tgt aac aaa gat        576
Pro Gly Lys Ala Asn Val Ser Ser Pro Val Lys Ser Cys Asn Lys Asp
    155                 160                 165 ggt gtc act gcc ctt agt gac agc aat gtc caa agt ggc tgt aac ggt        624
Gly Val Thr Ala Leu Ser Asp Ser Asn Val Gln Ser Gly Cys Asn Gly
170                 175                 180                 185 ggt aac agt tac atg tgt aac gac aac cag cct tgg gct gta aac gat        672
Gly Asn Ser Tyr Met Cys Asn Asp Asn Gln Pro Trp Ala Val Asn Asp
```

-continued

```
                190                 195                 200
aat ctt gcc tat ggt ttc gct gct gct gcc atc agt ggt ggt ggt gaa      720
Asn Leu Ala Tyr Gly Phe Ala Ala Ala Ala Ile Ser Gly Gly Gly Glu
            205                 210                 215 tct cgc tgg tgc tgt tct tgt ttc gaa ctt act ttc act tct acc tct      768
Ser Arg Trp Cys Cys Ser Cys Phe Glu Leu Thr Phe Thr Ser Thr Ser
        220                 225                 230 gtt gct ggt aag aag atg gtt atc caa gtc act aac act ggt ggt gat      816
Val Ala Gly Lys Lys Met Val Ile Gln Val Thr Asn Thr Gly Gly Asp
    235                 240                 245 ctt ggc tcc tct act ggt gct cac ttt gac ttg caa atg ccc ggt ggt      864
Leu Gly Ser Ser Thr Gly Ala His Phe Asp Leu Gln Met Pro Gly Gly
250                 255                 260                 265 ggt gtt ggt att ttc aat ggt tgc tcc aag caa tgg ggt gct ccc aat      912
Gly Val Gly Ile Phe Asn Gly Cys Ser Lys Gln Trp Gly Ala Pro Asn
                270                 275                 280 gac ggt tgg ggc tcg aga tac ggt ggt att tct tct gca tct gac tgc      960
Asp Gly Trp Gly Ser Arg Tyr Gly Gly Ile Ser Ser Ala Ser Asp Cys
            285                 290                 295 tct agt ctt cct tcc gca ctc caa gct ggt tgt aaa tgg aga ttc aac     1008
Ser Ser Leu Pro Ser Ala Leu Gln Ala Gly Cys Lys Trp Arg Phe Asn
        300                 305                 310 tgg ttc aag aac gct gat aac cca agc atg act tac aag gaa gtt acc     1056
Trp Phe Lys Asn Ala Asp Asn Pro Ser Met Thr Tyr Lys Glu Val Thr
    315                 320                 325 tgt ccc aag gaa atc acc gcc aag aca ggt tgt tca aga aaa taa        1101
Cys Pro Lys Glu Ile Thr Ala Lys Thr Gly Cys Ser Arg Lys
330                 335                 340

<210> SEQ ID NO 5
<211> LENGTH: 360
<212> TYPE: PRT
<213> ORGANISM: Rhizopus oryzae CP96001
<220> FEATURE:
<221> NAME/KEY: sig_peptide
<222> LOCATION: (-23)...(-1)
<220> FEATURE:
<221> NAME/KEY: mat_peptide
<222> LOCATION: (1)...(337)

<400> SEQUENCE: 5

Met Lys Phe Leu Thr Ile Ala Ser Ser Ala Ile Leu Ala Leu Ala Val
            -20                 -15                 -10

Gly Thr Glu Met Ala His Ala Ala Glu Cys Ser Lys Ala Tyr Tyr Gln
        -5                  1                   5

Cys Gly Gly Lys Asn Trp Asp Gly Pro Thr Cys Cys Glu Ser Gly Ser
10                  15                  20                  25

Thr Cys Val Asp Tyr Pro Asp Asn Pro Phe Tyr Ser Gln Cys Val Pro
                30                  35                  40

Asn Glu Asn Leu Thr Ser Thr Asn Lys Ser Ser His Lys Thr Thr Thr
            45                  50                  55

Thr Glu Ser Ala Lys Lys Thr Thr Thr Lys Gly Ser Lys Lys Thr
        60                  65                  70

Thr Thr Thr Glu Ala Ser Lys Lys Thr Thr Thr Glu Ala Ser Lys
    75                  80                  85

Lys Thr Thr Thr Thr Glu Ala Ser Lys Lys Thr Thr Thr Thr Lys
90                  95                  100                 105

Lys Ala Ser Thr Ser Thr Ser Ser Ser Ser Ser Ala Ser Thr Asn
                110                 115                 120
```

```
Tyr Ser Ala Val Ser Gly Gly Ala Ser Gly Asn Gly Glu Thr Thr Arg
            125                 130                 135

Tyr Trp Asp Cys Cys Lys Pro Ser Cys Ser Trp Pro Gly Lys Ala Asp
        140                 145                 150

Val Thr Ser Pro Val Gly Ser Cys Asn Lys Asp Gly Lys Thr Leu Ala
    155                 160                 165

Asp Asn Asn Thr Gln Asn Gly Cys Val Gly Gly Ser Ser Tyr Thr Cys
170                 175                 180                 185

Asn Asp Asn Gln Pro Trp Val Val Ser Asp Leu Ala Tyr Gly Phe
                190                 195                 200

Ala Ala Ala Ser Ile Ser Gly Gly Ser Glu Ala Thr Trp Cys Cys Ala
            205                 210                 215

Cys Phe Glu Leu Thr Phe Thr Ser Thr Ala Val Lys Gly Lys Lys Met
        220                 225                 230

Val Val Gln Val Thr Asn Thr Gly Ser Asp Leu Gly Ser Asn Thr Gly
    235                 240                 245

Ala His Phe Asp Leu Gln Met Pro Gly Gly Gly Val Gly Ile Tyr Asn
250                 255                 260                 265

Gly Cys Ala Thr Gln Trp Gly Ala Pro Thr Asp Gly Trp Gly Ala Arg
                270                 275                 280

Tyr Gly Val Ser Ser Ala Ser Asp Cys Ser Asn Leu Pro Ser Ala
            285                 290                 295

Leu Gln Ala Gly Cys Lys Trp Arg Phe Gly Trp Phe Lys Asn Ala Asp
        300                 305                 310

Asn Pro Thr Met Thr Tyr Lys Gln Val Thr Cys Pro Lys Ala Ile Thr
    315                 320                 325

Ala Lys Ser Gly Cys Ser Arg Lys
330                 335

<210> SEQ ID NO 6
<211> LENGTH: 1083
<212> TYPE: DNA
<213> ORGANISM: Rhizopus oryzae CP96001
<220> FEATURE:
<221> NAME/KEY: sig_peptide
<222> LOCATION: (1)...(69)
<220> FEATURE:
<221> NAME/KEY: mat_peptide
<222> LOCATION: (70)...(1083)

<400> SEQUENCE: 6 atg aag ttc ctt acc att gcc tcc tcc gct atc ttg gca ctt gcc gtc      48
Met Lys Phe Leu Thr Ile Ala Ser Ser Ala Ile Leu Ala Leu Ala Val
        -20                 -15                 -10 ggt act gaa atg gcc cat gct gct gaa tgt agc aag gct tac tac caa      96
Gly Thr Glu Met Ala His Ala Ala Glu Cys Ser Lys Ala Tyr Tyr Gln
    -5                   1               5 tgt ggt ggt aag aac tgg gat gga cct acc tgc tgt gaa tct ggc tct     144
Cys Gly Gly Lys Asn Trp Asp Gly Pro Thr Cys Cys Glu Ser Gly Ser
10                  15                  20                  25 act tgc gtt gat tat cct gac aat cct ttc tac tcc caa tgt gtt ccc     192
Thr Cys Val Asp Tyr Pro Asp Asn Pro Phe Tyr Ser Gln Cys Val Pro
                30                  35                  40 aat gaa aac ctc acc tcc act aac aaa tct tct cac aaa acc acc         240
Asn Glu Asn Leu Thr Ser Thr Asn Lys Ser Ser His Lys Thr Thr
            45                  50                  55 act gag agt gcc aag aag act acc act act aaa ggt tcc aag aag acc     288
Thr Glu Ser Ala Lys Lys Thr Thr Thr Thr Lys Gly Ser Lys Lys Thr
    60                  65                  70
```

```
acc act act gaa gcc tct aag aag acc acc act act gaa gct tcc aag        336
Thr Thr Thr Glu Ala Ser Lys Lys Thr Thr Thr Thr Glu Ala Ser Lys
         75                  80                  85 aag acc acc act act gaa gcc tct aag aag acc acc act act act aag        384
Lys Thr Thr Thr Thr Glu Ala Ser Lys Lys Thr Thr Thr Thr Thr Lys
 90                  95                 100                 105 aag gct tct acc tcc act tcc tct tcc tct tct gct tct aca aac            432
Lys Ala Ser Thr Ser Thr Ser Ser Ser Ser Ser Ala Ser Thr Asn
                110                 115                 120 tac tcc gct gtc tct ggt ggt gcc tcc ggt aat ggt gaa acc act cgc        480
Tyr Ser Ala Val Ser Gly Gly Ala Ser Gly Asn Gly Glu Thr Thr Arg
             125                 130                 135 tac tgg gat tgt tgt aag cct tct tgc agt tgg ccc ggt aag gct gat        528
Tyr Trp Asp Cys Cys Lys Pro Ser Cys Ser Trp Pro Gly Lys Ala Asp
             140                 145                 150 gtc acc tcc cct gtt ggc tcc tgt aac aag gat ggt aag act ctt gct        576
Val Thr Ser Pro Val Gly Ser Cys Asn Lys Asp Gly Lys Thr Leu Ala
         155                 160                 165 gat aac aac act caa aac ggc tgt gtt ggt ggt agc agc tac acc tgt        624
Asp Asn Asn Thr Gln Asn Gly Cys Val Gly Gly Ser Ser Tyr Thr Cys
170                 175                 180                 185 aat gac aat caa cct tgg gtt gtt agc gac gac ctt gcc tac ggt ttc        672
Asn Asp Asn Gln Pro Trp Val Val Ser Asp Asp Leu Ala Tyr Gly Phe
                190                 195                 200 gcc gct gct tcc att tct ggt ggt agc gaa gct act tgg tgt tgt gcc        720
Ala Ala Ala Ser Ile Ser Gly Gly Ser Glu Ala Thr Trp Cys Cys Ala
             205                 210                 215 tgt ttc gaa ctc aca ttc acc tct act gcc gtc aag ggt aag aag atg        768
Cys Phe Glu Leu Thr Phe Thr Ser Thr Ala Val Lys Gly Lys Lys Met
         220                 225                 230 gtt gtt caa gta acc aac act ggt tct gac ctt ggc tct aac act ggt        816
Val Val Gln Val Thr Asn Thr Gly Ser Asp Leu Gly Ser Asn Thr Gly
235                 240                 245 gct cac ttt gac ttg caa atg ccc ggt ggt ggt gtt ggt atc tac aat        864
Ala His Phe Asp Leu Gln Met Pro Gly Gly Gly Val Gly Ile Tyr Asn
250                 255                 260                 265 ggt tgt gcc act caa tgg ggt gct ccc acc gat ggt tgg ggt gca aga        912
Gly Cys Ala Thr Gln Trp Gly Ala Pro Thr Asp Gly Trp Gly Ala Arg
             270                 275                 280 tac ggc ggt gtt tct tct gcc tct gac tgt tct aac ctt cct tct gcc        960
Tyr Gly Gly Val Ser Ser Ala Ser Asp Cys Ser Asn Leu Pro Ser Ala
             285                 290                 295 ctt caa gct ggt tgt aag tgg aga ttc ggc tgg ttc aaa aac gct gat       1008
Leu Gln Ala Gly Cys Lys Trp Arg Phe Gly Trp Phe Lys Asn Ala Asp
         300                 305                 310 aac cca acc atg acc tac aaa caa gtt acc tgt ccc aag gct atc act       1056
Asn Pro Thr Met Thr Tyr Lys Gln Val Thr Cys Pro Lys Ala Ile Thr
315                 320                 325 gcc aag tct ggc tgt tca aga aaa taa                                   1083
Ala Lys Ser Gly Cys Ser Arg Lys
330                 335

<210> SEQ ID NO 7
<211> LENGTH: 338
<212> TYPE: PRT
<213> ORGANISM: Mucor circinelloides CP99001
<220> FEATURE:
<221> NAME/KEY: sig_peptide
<222> LOCATION: (-22)...(-1)
<220> FEATURE:
<221> NAME/KEY: mat_peptide
```

<222> LOCATION: (1)...(316)

<400> SEQUENCE: 7

Met Lys Phe Thr Val Ala Ile Thr Ser Ile Ala Val Ala Leu Ala Leu
    -20                 -15                 -10

Ser Ser Ser Ala Glu Ala Ala Ser Cys Ser Ser Val Tyr Gly Gln Cys
 -5               1               5                        10

Gly Gly Ile Gly Trp Ser Gly Pro Thr Cys Cys Glu Ser Gly Ser Thr
            15                  20                  25

Cys Val Ala Gln Glu Gly Asn Lys Tyr Tyr Ser Gln Cys Leu Pro Gly
        30                  35                  40

Ser His Ser Asn Asn Ala Gly Asn Ala Ser Ser Thr Lys Lys Thr Ser
        45                  50                  55

Thr Lys Thr Ser Thr Thr Thr Ala Lys Ala Thr Ala Thr Val Thr Thr
60                  65                  70                  75

Lys Thr Val Thr Lys Thr Thr Thr Lys Thr Thr Thr Lys Thr Ser Thr
                80                  85                  90

Thr Ala Ala Ala Ser Thr Ser Thr Ser Ser Ser Ala Gly Tyr Lys Val
                95                  100                 105

Ile Ser Gly Gly Lys Ser Gly Ser Gly Ser Thr Thr Arg Tyr Trp Asp
            110                 115                 120

Cys Cys Lys Ala Ser Cys Ser Trp Pro Gly Lys Ala Ser Val Thr Gly
        125                 130                 135

Pro Val Asp Thr Cys Ala Ser Asn Gly Ile Ser Leu Leu Asp Ala Asn
140                 145                 150                 155

Ala Gln Ser Gly Cys Asn Gly Gly Asn Gly Phe Met Cys Asn Asn Asn
                160                 165                 170

Gln Pro Trp Ala Val Asn Asp Glu Leu Ala Tyr Gly Phe Ala Ala Ala
            175                 180                 185

Ser Ile Ala Gly Ser Asn Glu Ala Gly Trp Cys Cys Gly Cys Tyr Glu
        190                 195                 200

Leu Thr Phe Thr Ser Gly Ala Ala Ser Gly Lys Lys Met Val Val Gln
    205                 210                 215

Val Thr Asn Thr Gly Gly Asp Leu Gly Ser Asn His Phe Asp Leu Gln
220                 225                 230                 235

Met Pro Gly Gly Gly Val Gly Ile Phe Asn Gly Cys Ala Ala Gln Trp
                240                 245                 250

Gly Ala Pro Asn Asp Gly Trp Gly Ala Arg Tyr Gly Gly Val Ser Ser
            255                 260                 265

Val Ser Asp Cys Ala Ser Leu Pro Ser Ala Leu Gln Ala Gly Cys Lys
        270                 275                 280

Trp Arg Phe Asn Trp Phe Lys Asn Ser Asp Asn Pro Thr Met Thr Phe
    285                 290                 295

Lys Glu Val Thr Cys Pro Ala Glu Leu Thr Thr Arg Ser Gly Cys Glu
300                 305                 310                 315

Arg Lys

<210> SEQ ID NO 8
<211> LENGTH: 1017
<212> TYPE: DNA
<213> ORGANISM: Mucor circinelloides CP99001
<220> FEATURE:
<221> NAME/KEY: sig_peptide
<222> LOCATION: (1)...(66)
<220> FEATURE:
<221> NAME/KEY: mat_peptide -continued

```
<222> LOCATION: (67)...(1017)

<400> SEQUENCE: 8 atg aag ttc acc gtt gct att act tca atc gct gtt gca ctc gct ctc         48
Met Lys Phe Thr Val Ala Ile Thr Ser Ile Ala Val Ala Leu Ala Leu
    -20                 -15                 -10 agc tct tct gct gaa gct gct tct tgc agc tct gtc tat ggt caa tgt         96
Ser Ser Ser Ala Glu Ala Ala Ser Cys Ser Ser Val Tyr Gly Gln Cys
 -5                   1               5                  10 ggt ggc att gga tgg agt gga cct acc tgt tgt gaa agt ggc tct act        144
Gly Gly Ile Gly Trp Ser Gly Pro Thr Cys Cys Glu Ser Gly Ser Thr
             15                  20                  25 tgc gtt gct caa gaa ggc aac aaa tac tac tct caa tgt ctt ccc gga        192
Cys Val Ala Gln Glu Gly Asn Lys Tyr Tyr Ser Gln Cys Leu Pro Gly
         30                  35                  40 tcc cac agt aac aat gct ggt aac gct agc agc acc aag aag aca tct        240
Ser His Ser Asn Asn Ala Gly Asn Ala Ser Ser Thr Lys Lys Thr Ser
     45                  50                  55 acc aag aca tct act acc acc gcc aag gct act gct act gtc acc acc        288
Thr Lys Thr Ser Thr Thr Thr Ala Lys Ala Thr Ala Thr Val Thr Thr
 60                  65                  70                  75 aag aca gta acc aag aca act acc aag aca act acc aag act agc act        336
Lys Thr Val Thr Lys Thr Thr Thr Lys Thr Thr Thr Lys Thr Ser Thr
                 80                  85                  90 act gcc gct gct tct act tcc acc tct tct tct gct ggt tac aag gtc        384
Thr Ala Ala Ala Ser Thr Ser Thr Ser Ser Ser Ala Gly Tyr Lys Val
             95                 100                 105 atc tct ggc ggt aaa tct ggc agt ggt tcc aca act cgt tat tgg gat        432
Ile Ser Gly Gly Lys Ser Gly Ser Gly Ser Thr Thr Arg Tyr Trp Asp
         110                 115                 120 tgt tgt aaa gct tct tgc agc tgg cct gga aaa gct tct gtc act ggt        480
Cys Cys Lys Ala Ser Cys Ser Trp Pro Gly Lys Ala Ser Val Thr Gly
     125                 130                 135 cct gtt gac acc tgt gcc tcc aat ggt atc tct tta tta gat gcc aat        528
Pro Val Asp Thr Cys Ala Ser Asn Gly Ile Ser Leu Leu Asp Ala Asn
140                 145                 150                 155 gct caa agt ggt tgt aac ggt ggt aat ggt ttc atg tgt aac aac aac        576
Ala Gln Ser Gly Cys Asn Gly Gly Asn Gly Phe Met Cys Asn Asn Asn
                160                 165                 170 caa cct tgg gct gtc aat gat gag ctc gct tac ggt ttc gct gct gcc        624
Gln Pro Trp Ala Val Asn Asp Glu Leu Ala Tyr Gly Phe Ala Ala Ala
            175                 180                 185 tct att gct ggc tcc aac gaa gct gga tgg tgt tgt ggc tgt tat gaa        672
Ser Ile Ala Gly Ser Asn Glu Ala Gly Trp Cys Cys Gly Cys Tyr Glu
        190                 195                 200 ttg acc ttc act tct ggc gct gct tct gga aag aag atg gtt gtt caa        720
Leu Thr Phe Thr Ser Gly Ala Ala Ser Gly Lys Lys Met Val Val Gln
205                 210                 215 gtt acc aac acc ggt ggc gat tta ggc tct aac cac ttt gat ttg caa        768
Val Thr Asn Thr Gly Gly Asp Leu Gly Ser Asn His Phe Asp Leu Gln
220                 225                 230                 235 atg ccc ggt ggt ggc gtt ggt atc ttc aat ggc tgt gct gct caa tgg        816
Met Pro Gly Gly Gly Val Gly Ile Phe Asn Gly Cys Ala Ala Gln Trp
                240                 245                 250 ggc gct ccc aat gat ggc tgg gga gct aga tat ggt ggt gtc agc tct        864
Gly Ala Pro Asn Asp Gly Trp Gly Ala Arg Tyr Gly Gly Val Ser Ser
            255                 260                 265 gtc tct gac tgt gcc tct ctt ccc tct gct ctt caa gct ggt tgt aaa        912
Val Ser Asp Cys Ala Ser Leu Pro Ser Ala Leu Gln Ala Gly Cys Lys
        270                 275                 280
```

-continued

```
tgg aga ttc aac tgg ttc aag aac tct gat aac cct acc atg acc ttc      960
Trp Arg Phe Asn Trp Phe Lys Asn Ser Asp Asn Pro Thr Met Thr Phe
    285                 290                 295 aag gaa gtt acc tgt cct gct gaa tta act act cgc tca ggt tgc gaa     1008
Lys Glu Val Thr Cys Pro Ala Glu Leu Thr Thr Arg Ser Gly Cys Glu
300                 305                 310                 315 aga aag taa                                                         1017
Arg Lys
```

<210> SEQ ID NO 9
<211> LENGTH: 387
<212> TYPE: PRT
<213> ORGANISM: Mucor circinelloides CP99001
<220> FEATURE:
<221> NAME/KEY: sig_peptide
<222> LOCATION: (-22)...(-1)
<220> FEATURE:
<221> NAME/KEY: mat_peptide
<222> LOCATION: (1)...(365)

<400> SEQUENCE: 9

```
Met Lys Phe Thr Val Ala Ile Thr Ser Ile Ala Val Ala Leu Ala Leu
        -20                 -15                 -10

Ser Ser Ser Ala Glu Ala Ala Ser Cys Ser Ser Val Tyr Gly Gln Cys
    -5                   1               5                  10

Gly Gly Ile Gly Trp Thr Gly Pro Thr Cys Cys Asp Ala Gly Ser Thr
                15                  20                  25

Cys Lys Ala Gln Lys Asp Asn Lys Tyr Tyr Ser Gln Cys Ile Pro Lys
            30                  35                  40

Pro Lys Gly Ser Ser Ser Ser Ser Cys Ser Ser Val Tyr Ser Gln
        45                  50                  55

Cys Gly Gly Ile Gly Trp Ser Gly Pro Thr Cys Cys Glu Ser Gly Ser
 60                  65                  70

Thr Cys Val Ala Gln Glu Gly Asn Lys Tyr Tyr Ser Gln Cys Leu Pro
75                  80                  85                  90

Gly Ser His Ser Asn Asn Ala Gly Asn Ala Ser Ser Thr Lys Lys Thr
                95                  100                 105

Ser Thr Lys Thr Ser Thr Thr Thr Ala Lys Ala Thr Ala Thr Val Thr
            110                 115                 120

Thr Lys Thr Val Thr Lys Thr Thr Thr Lys Thr Thr Thr Lys Thr Ser
        125                 130                 135

Thr Thr Ala Ala Ala Ser Thr Ser Thr Ser Ser Ala Gly Tyr Lys
    140                 145                 150

Val Ile Ser Gly Gly Lys Ser Gly Ser Gly Ser Thr Thr Arg Tyr Trp
155                 160                 165                 170

Asp Cys Cys Lys Ala Ser Cys Ser Trp Pro Gly Lys Ala Ser Val Thr
                175                 180                 185

Gly Pro Val Asp Thr Cys Ala Ser Asn Gly Ile Ser Leu Leu Asp Ala
            190                 195                 200

Asn Ala Gln Ser Gly Cys Asn Gly Gly Asn Gly Phe Met Cys Asn Asn
        205                 210                 215

Asn Gln Pro Trp Ala Val Asn Asp Glu Leu Ala Tyr Gly Phe Ala Ala
    220                 225                 230

Ala Ser Ile Ala Gly Ser Asn Glu Ala Gly Trp Cys Cys Gly Cys Tyr
235                 240                 245                 250

Glu Leu Thr Phe Thr Ser Gly Ala Ala Ser Gly Lys Lys Met Val Val
                255                 260                 265
```

```
Gln Val Thr Asn Thr Gly Gly Asp Leu Gly Ser Asn His Phe Asp Leu
            270                 275                 280

Gln Met Pro Gly Gly Val Gly Ile Phe Asn Gly Cys Ala Ala Gln
            285                 290                 295

Trp Gly Ala Pro Asn Asp Gly Trp Gly Ala Arg Tyr Gly Gly Val Ser
            300                 305                 310

Ser Val Ser Asp Cys Ala Ser Leu Pro Ser Ala Leu Gln Ala Gly Cys
315                 320                 325                 330

Lys Trp Arg Phe Asn Trp Phe Lys Asn Ser Asp Asn Pro Thr Met Thr
                335                 340                 345

Phe Lys Glu Val Thr Cys Pro Ala Glu Leu Thr Thr Arg Ser Gly Cys
            350                 355                 360

Glu Arg Lys
        365

<210> SEQ ID NO 10
<211> LENGTH: 1164
<212> TYPE: DNA
<213> ORGANISM: Mucor circinelloides CP99001
<220> FEATURE:
<221> NAME/KEY: sig_peptide
<222> LOCATION: (1)...(66)
<220> FEATURE:
<221> NAME/KEY: mat_peptide
<222> LOCATION: (67)...(1164)

<400> SEQUENCE: 10 atg aag ttc acc gtt gct att act tca atc gct gtt gca ctc gct ctc      48
Met Lys Phe Thr Val Ala Ile Thr Ser Ile Ala Val Ala Leu Ala Leu
        -20                 -15                 -10 agc tct tct gct gaa gct gct tct tgc agc tct gtc tat ggt caa tgt      96
Ser Ser Ser Ala Glu Ala Ala Ser Cys Ser Ser Val Tyr Gly Gln Cys
            -5                   1               5              10 ggc ggc att ggc tgg act ggt cct aca tgt tgt gat gct gga tcg acc     144
Gly Gly Ile Gly Trp Thr Gly Pro Thr Cys Cys Asp Ala Gly Ser Thr
                15                  20                  25 tgt aaa gct caa aag gat aac aaa tat tat tct caa tgt att ccc aaa     192
Cys Lys Ala Gln Lys Asp Asn Lys Tyr Tyr Ser Gln Cys Ile Pro Lys
            30                  35                  40 ccc aag ggt tcc tcc tca tca tca tgt agt tcc gtc tat agt caa         240
Pro Lys Gly Ser Ser Ser Ser Ser Cys Ser Ser Val Tyr Ser Gln
            45                  50                  55 tgc ggt ggc att gga tgg agt gga cct acc tgt tgt gaa agt ggc tct     288
Cys Gly Gly Ile Gly Trp Ser Gly Pro Thr Cys Cys Glu Ser Gly Ser
            60                  65                  70 act tgc gtt gct caa gaa ggc aac aaa tac tac tct caa tgt ctt ccc     336
Thr Cys Val Ala Gln Glu Gly Asn Lys Tyr Tyr Ser Gln Cys Leu Pro
75                  80                  85                  90 gga tcc cac agt aac aat gct ggt aac gct agc agc acc aag aag aca     384
Gly Ser His Ser Asn Asn Ala Gly Asn Ala Ser Ser Thr Lys Lys Thr
                95                  100                 105 tct acc aag aca tct act acc acc gcc aag gct act gct act gtc acc     432
Ser Thr Lys Thr Ser Thr Thr Thr Ala Lys Ala Thr Ala Thr Val Thr
            110                 115                 120 acc aag aca gta acc aag aca act acc aag aca act acc aag act agc     480
Thr Lys Thr Val Thr Lys Thr Thr Thr Lys Thr Thr Thr Lys Thr Ser
            125                 130                 135 act act gcc gct gct tct act tcc acc tct tct tct gct ggt tac aag     528
Thr Thr Ala Ala Ala Ser Thr Ser Thr Ser Ser Ser Ala Gly Tyr Lys
            140                 145                 150
```

```
gtc atc tct ggc ggt aaa tct ggc agt ggt tcc aca act cgt tat tgg       576
Val Ile Ser Gly Gly Lys Ser Gly Ser Gly Ser Thr Thr Arg Tyr Trp
155                 160                 165                 170 gat tgt tgt aaa gct tct tgc agc tgg cct gga aaa gct tct gtc act       624
Asp Cys Cys Lys Ala Ser Cys Ser Trp Pro Gly Lys Ala Ser Val Thr
            175                 180                 185 ggt cct gtt gac acc tgt gcc tcc aat ggt atc tct tta tta gat gcc       672
Gly Pro Val Asp Thr Cys Ala Ser Asn Gly Ile Ser Leu Leu Asp Ala
        190                 195                 200 aat gct caa agt ggt tgt aac ggt ggt aat ggt ttc atg tgt aac aac       720
Asn Ala Gln Ser Gly Cys Asn Gly Gly Asn Gly Phe Met Cys Asn Asn
    205                 210                 215 aac caa cct tgg gct gtc aat gat gag ctc gct tac ggt ttc gct gct       768
Asn Gln Pro Trp Ala Val Asn Asp Glu Leu Ala Tyr Gly Phe Ala Ala
220                 225                 230 gcc tct att gct ggc tcc aac gaa gct gga tgg tgt tgt ggc tgt tat       816
Ala Ser Ile Ala Gly Ser Asn Glu Ala Gly Trp Cys Cys Gly Cys Tyr
235                 240                 245                 250 gaa ttg acc ttc act tct ggc gct gct tct gga aag aag atg gtt gtt       864
Glu Leu Thr Phe Thr Ser Gly Ala Ala Ser Gly Lys Lys Met Val Val
            255                 260                 265 caa gtt acc aac acc ggt ggc gat tta ggc tct aac cac ttt gat ttg       912
Gln Val Thr Asn Thr Gly Gly Asp Leu Gly Ser Asn His Phe Asp Leu
        270                 275                 280 caa atg ccc ggt ggt ggc gtt ggt atc ttc aat ggc tgt gct gct caa       960
Gln Met Pro Gly Gly Gly Val Gly Ile Phe Asn Gly Cys Ala Ala Gln
    285                 290                 295 tgg ggc gct ccc aat gat ggc tgg gga gct aga tat ggt ggt gtc agc      1008
Trp Gly Ala Pro Asn Asp Gly Trp Gly Ala Arg Tyr Gly Gly Val Ser
300                 305                 310 tct gtc tct gac tgt gcc tct ctt ccc tct gct ctt caa gct ggt tgt      1056
Ser Val Ser Asp Cys Ala Ser Leu Pro Ser Ala Leu Gln Ala Gly Cys
315                 320                 325                 330 aaa tgg aga ttc aac tgg ttc aag aac tct gat aac cct acc atg acc      1104
Lys Trp Arg Phe Asn Trp Phe Lys Asn Ser Asp Asn Pro Thr Met Thr
            335                 340                 345 ttc aag gaa gtt acc tgt cct gct gaa tta act act cgc tca ggt tgc      1152
Phe Lys Glu Val Thr Cys Pro Ala Glu Leu Thr Thr Arg Ser Gly Cys
        350                 355                 360 gaa aga aag taa                                                       1164
Glu Arg Lys
        365

<210> SEQ ID NO 11
<211> LENGTH: 346
<212> TYPE: PRT
<213> ORGANISM: Phycomyces nitens CP99002
<220> FEATURE:
<221> NAME/KEY: sig_peptide
<222> LOCATION: (-19)...(-1)
<220> FEATURE:
<221> NAME/KEY: mat_peptide
<222> LOCATION: (1)...(327)

<400> SEQUENCE: 11

Met Lys Phe Ser Ile Ile Ala Ser Ala Leu Leu Leu Ala Ala Ser Ser
                -15                 -10                  -5

Thr Tyr Ala Ala Glu Cys Ser Gln Gly Tyr Gly Gln Cys Gly Gly Lys
         1                   5                  10

Met Trp Thr Gly Pro Thr Cys Cys Thr Ser Gly Phe Thr Cys Val Gly
 15                  20                  25
```

```
Ala Glu Asn Asn Glu Trp Tyr Ser Gln Cys Ile Pro Asn Asp Gln Val
 30                  35                  40                  45

Gln Gly Asn Pro Lys Thr Thr Thr Thr Thr Thr Lys Ala Ala Thr
             50                  55                  60

Thr Thr Lys Ala Pro Val Thr Thr Thr Lys Ala Thr Thr Thr Thr
             65                  70                  75

Thr Lys Ala Pro Val Thr Thr Thr Lys Ala Thr Thr Thr Thr Thr
         80                  85                  90

Lys Thr Thr Thr Lys Thr Thr Thr Lys Ala Ala Thr Thr Thr Ser
     95                 100                 105

Ser Ser Asn Thr Gly Tyr Ser Pro Ile Ser Gly Gly Phe Ser Gly Asn
110                 115                 120                 125

Gly Arg Thr Thr Arg Tyr Trp Asp Cys Cys Lys Pro Ser Cys Ala Trp
                130                 135                 140

Asp Gly Lys Ala Ser Val Thr Lys Pro Val Leu Thr Cys Ala Lys Asp
                145                 150                 155

Gly Val Ser Arg Leu Gly Ser Asp Val Gln Ser Gly Cys Val Gly Gly
                160                 165                 170

Gln Ala Tyr Met Cys Asn Asp Asn Gln Pro Trp Val Val Asn Asp Asp
175                 180                 185

Leu Ala Tyr Gly Phe Ala Ala Ser Leu Gly Ser Ala Gly Ala Ser
190                 195                 200                 205

Ala Phe Cys Cys Gly Cys Tyr Glu Leu Thr Phe Thr Asn Thr Ala Val
                210                 215                 220

Ala Gly Lys Lys Phe Val Val Gln Val Thr Asn Thr Gly Asp Asp Leu
                225                 230                 235

Ser Thr Asn His Phe Asp Leu Gln Met Pro Gly Gly Gly Val Gly Tyr
                240                 245                 250

Phe Asn Gly Cys Gln Ser Gln Trp Asn Thr Asn Thr Asp Gly Trp Gly
255                 260                 265

Ala Arg Tyr Gly Gly Ile Ser Ser Ile Ser Glu Cys Asp Lys Leu Pro
270                 275                 280                 285

Thr Gln Leu Gln Ala Gly Cys Lys Trp Arg Phe Gly Trp Phe Lys Asn
                290                 295                 300

Ala Asp Asn Pro Glu Val Thr Phe Lys Ala Val Thr Cys Pro Ala Glu
                305                 310                 315

Ile Ile Ala Lys Thr Gly Cys Glu Arg Lys
        320                 325

<210> SEQ ID NO 12
<211> LENGTH: 1041
<212> TYPE: DNA
<213> ORGANISM: Phycomyces nitens CP99002
<220> FEATURE:
<221> NAME/KEY: sig_peptide
<222> LOCATION: (1)...(57)
<220> FEATURE:
<221> NAME/KEY: mat_peptide
<222> LOCATION: (58)...(1041)

<400> SEQUENCE: 12 atg aag ttc tcc atc atc gct tcc gcc ctt ctc ctc gct gcc agc tcc      48
Met Lys Phe Ser Ile Ile Ala Ser Ala Leu Leu Leu Ala Ala Ser Ser
            -15                 -10                  -5 act tac gct gct gaa tgc agc caa ggc tat ggc cag tgt ggt ggc aag      96
Thr Tyr Ala Ala Glu Cys Ser Gln Gly Tyr Gly Gln Cys Gly Gly Lys
                 1               5                  10
```

-continued

```
atg tgg act ggt ccc acc tgc tgc acc tcc ggc ttc acc tgt gta ggt      144
Met Trp Thr Gly Pro Thr Cys Cys Thr Ser Gly Phe Thr Cys Val Gly
 15                  20                  25 gcc gaa aac aac gag tgg tac tct cag tgt atc ccc aac gat caa gtc      192
Ala Glu Asn Asn Glu Trp Tyr Ser Gln Cys Ile Pro Asn Asp Gln Val
 30                  35                  40                  45 cag ggt aac ccc aag acc acc acc acc acc acc aag gct gcc act          240
Gln Gly Asn Pro Lys Thr Thr Thr Thr Thr Thr Lys Ala Ala Thr
                 50                  55                  60 acc acc aag gct cct gtc acc acc acc aag gcc acc acc acc acc          288
Thr Thr Lys Ala Pro Val Thr Thr Thr Lys Ala Thr Thr Thr Thr
             65                  70                  75 acc aag gcc cct gtc acc acc acc aag gcc act act act acc acc acc      336
Thr Lys Ala Pro Val Thr Thr Thr Lys Ala Thr Thr Thr Thr Thr Thr
         80                  85                  90 aag acc acc acc aag acc acc acc aag gct gcc acc acc acc tcc          384
Lys Thr Thr Thr Lys Thr Thr Thr Lys Ala Ala Thr Thr Thr Ser
     95                 100                 105 tct tcc aac act ggc tac agc ccc att tct ggt ggc ttc tct gga aac      432
Ser Ser Asn Thr Gly Tyr Ser Pro Ile Ser Gly Gly Phe Ser Gly Asn
110                 115                 120                 125 ggt cgc act acc cgc tac tgg gat tgc tgc aag ccc tct tgc gcc tgg      480
Gly Arg Thr Thr Arg Tyr Trp Asp Cys Cys Lys Pro Ser Cys Ala Trp
                130                 135                 140 gac gga aag gct tct gta act aag cct gta ctc acc tgt gcc aag gat      528
Asp Gly Lys Ala Ser Val Thr Lys Pro Val Leu Thr Cys Ala Lys Asp
            145                 150                 155 ggt gtc agc cgt ctc ggt tcc gat gtc cag agc ggt tgc gtc ggc ggc      576
Gly Val Ser Arg Leu Gly Ser Asp Val Gln Ser Gly Cys Val Gly Gly
        160                 165                 170 cag gcc tac atg tgc aat gac aac cag ccc tgg gtt gtc aat gac gac      624
Gln Ala Tyr Met Cys Asn Asp Asn Gln Pro Trp Val Val Asn Asp Asp
    175                 180                 185 ctt gcc tac ggt ttc gct gct gcc agt ctc ggt agc gcc ggt gcc tct      672
Leu Ala Tyr Gly Phe Ala Ala Ala Ser Leu Gly Ser Ala Gly Ala Ser
190                 195                 200                 205 gca ttc tgc tgc ggc tgt tac gag ctt acc ttc acc aac act gct gtc      720
Ala Phe Cys Cys Gly Cys Tyr Glu Leu Thr Phe Thr Asn Thr Ala Val
                210                 215                 220 gct ggc aag aag ttt gtc gtc cag gtc acc aac acc ggt gat gat ctc      768
Ala Gly Lys Lys Phe Val Val Gln Val Thr Asn Thr Gly Asp Asp Leu
            225                 230                 235 agc acc aac cac ttt gat ttg cag atg ccc ggc ggt ggt gtc ggc tac      816
Ser Thr Asn His Phe Asp Leu Gln Met Pro Gly Gly Gly Val Gly Tyr
        240                 245                 250 ttc aac ggc tgc cag tcc cag tgg aac acc aac acc gat ggc tgg ggt      864
Phe Asn Gly Cys Gln Ser Gln Trp Asn Thr Asn Thr Asp Gly Trp Gly
    255                 260                 265 gct cgc tat ggc ggt att agc tct att tca gag tgc gac aag ctt cct      912
Ala Arg Tyr Gly Gly Ile Ser Ser Ile Ser Glu Cys Asp Lys Leu Pro
270                 275                 280                 285 acc cag ttg cag gct ggt tgc aag tgg aga ttc gga tgg ttc aag aac      960
Thr Gln Leu Gln Ala Gly Cys Lys Trp Arg Phe Gly Trp Phe Lys Asn
                290                 295                 300 gct gac aac cca gag gtc acc ttc aag gct gtt act tgc cct gcc gag     1008
Ala Asp Asn Pro Glu Val Thr Phe Lys Ala Val Thr Cys Pro Ala Glu
            305                 310                 315 atc att gcc aag act ggt tgc gag cgc aag taa                         1041
Ile Ile Ala Lys Thr Gly Cys Glu Arg Lys
```

<210> SEQ ID NO 13
<211> LENGTH: 1043
<212> TYPE: DNA
<213> ORGANISM: Artificial Sequence
<220> FEATURE:
<223> OTHER INFORMATION: Codon-optimized sequence corresponding to RCE I
    protein (SEQ.ID NO: 2)
<220> FEATURE:
<221> NAME/KEY: sig_peptide
<222> LOCATION: (16)...(84)
<220> FEATURE:
<221> NAME/KEY: mat_peptide
<222> LOCATION: (84)...(1043)

<400> SEQUENCE: 13

```
ggatcctggg acaag atg aag ttc atc act atc gcc tcc tcc gcc ctc ctt        51
            Met Lys Phe Ile Thr Ile Ala Ser Ser Ala Leu Leu
                -20              -15 gcc ctc gcc ctt ggc act gag atg gcc tcc gct gag tgc tcc aag              99
Ala Leu Ala Leu Gly Thr Glu Met Ala Ser Ala Glu Cys Ser Lys
         -10              -5               1               5 ctc tac gga cag tgc ggc gga aag aac tgg aac ggc ccc acc tgc tgc         147
Leu Tyr Gly Gln Cys Gly Gly Lys Asn Trp Asn Gly Pro Thr Cys Cys
                 10              15              20 gag agc ggc tcg acc tgc aag gtc tcg aat gac tac tac agc cag tgc         195
Glu Ser Gly Ser Thr Cys Lys Val Ser Asn Asp Tyr Tyr Ser Gln Cys
         25              30              35 ctg ccg agc ggc tcc tcg gga aac aag tcg agc gag tcg gcc cac aag         243
Leu Pro Ser Gly Ser Ser Gly Asn Lys Ser Ser Glu Ser Ala His Lys
         40              45              50 aag acc acg acc gct gcc cac aag aag acc acg acc gcc gct cac aag         291
Lys Thr Thr Thr Ala Ala His Lys Lys Thr Thr Thr Ala Ala His Lys
         55              60              65 aag act acg acc gct ccc gcc aag aag acc acg acc gtc gcc aag gct         339
Lys Thr Thr Thr Ala Pro Ala Lys Lys Thr Thr Thr Val Ala Lys Ala
70               75              80              85 tcg act ccg tcc aac tcg agc agc tcg tct tcg gga aag tac agc gct         387
Ser Thr Pro Ser Asn Ser Ser Ser Ser Ser Gly Lys Tyr Ser Ala
                 90              95              100 gtc agc ggt ggc gct agc ggc aac ggc gtc act acc cgc tac tgg gac         435
Val Ser Gly Gly Ala Ser Gly Asn Gly Val Thr Thr Arg Tyr Trp Asp
         105             110             115 tgc tgc aag gct tcg tgc tcg tgg ccc ggc aag gct aac gtc agc tcg         483
Cys Cys Lys Ala Ser Cys Ser Trp Pro Gly Lys Ala Asn Val Ser Ser
         120             125             130 cct gtc aag tcc tgc aac aag gac ggc gtc acc gct ctt agc gac tcc         531
Pro Val Lys Ser Cys Asn Lys Asp Gly Val Thr Ala Leu Ser Asp Ser
         135             140             145 aac gcc cag tcc ggc tgc aac ggc ggc aac tcc tac atg tgc aac gac         579
Asn Ala Gln Ser Gly Cys Asn Gly Gly Asn Ser Tyr Met Cys Asn Asp
150              155             160             165 aac cag cca tgg gct gtc aac gac aac ctt gct tac ggt ttc gct gcc         627
Asn Gln Pro Trp Ala Val Asn Asp Asn Leu Ala Tyr Gly Phe Ala Ala
                 170             175             180 gct gcc att agc ggc ggt ggc gag agc cgc tgg tgc tgc tcc tgc ttc         675
Ala Ala Ile Ser Gly Gly Gly Glu Ser Arg Trp Cys Cys Ser Cys Phe
         185             190             195 gag ctc acc ttc acc tcc acc agc gtt gct ggc aag aag atg gtc gtc         723
Glu Leu Thr Phe Thr Ser Thr Ser Val Ala Gly Lys Lys Met Val Val
         200             205             210
```

```
cag gtc acc aac act ggc ggt gac ctt ggc agc tcg acc ggt gcc cac      771
Gln Val Thr Asn Thr Gly Gly Asp Leu Gly Ser Ser Thr Gly Ala His
    215                 220                 225 ttc gat ctc cag atg ccc ggc ggc gtc ggc atc ttc aac gga tgc          819
Phe Asp Leu Gln Met Pro Gly Gly Val Gly Ile Phe Asn Gly Cys
230                 235                 240                 245 tcg tcc cag tgg ggc gct ccc aac gac ggc tgg ggc tcg cgc tac ggc      867
Ser Ser Gln Trp Gly Ala Pro Asn Asp Gly Trp Gly Ser Arg Tyr Gly
                250                 255                 260 ggc atc agc tcc gcc agc gac tgc tcg tcc ctc ccc agc gcc ctc cag      915
Gly Ile Ser Ser Ala Ser Asp Cys Ser Ser Leu Pro Ser Ala Leu Gln
            265                 270                 275 gcc ggc tgc aag tgg cgc ttc aac tgg ttc aag aac gcc gac aac ccg      963
Ala Gly Cys Lys Trp Arg Phe Asn Trp Phe Lys Asn Ala Asp Asn Pro
        280                 285                 290 tcc atg acc tac aag gag gtc acc tgc ccc aag gag atc acc gct aag      1011
Ser Met Thr Tyr Lys Glu Val Thr Cys Pro Lys Glu Ile Thr Ala Lys
    295                 300                 305 acc gga tgc tcg cgc aag taa acgcagg atcc                             1043
Thr Gly Cys Ser Arg Lys
310                 315

<210> SEQ ID NO 14
<211> LENGTH: 40
<212> TYPE: PRT
<213> ORGANISM: Rhizopus oryzae CP96001

<400> SEQUENCE: 14

Ala Glu Cys Ser Lys Leu Tyr Gly Gln Cys Gly Gly Lys Asn Trp Asn
1               5                   10                  15

Gly Pro Thr Cys Cys Glu Ser Gly Ser Thr Cys Lys Val Ser Asn Asp
            20                  25                  30

Tyr Tyr Ser Gln Cys Leu Pro Ser
        35                  40

<210> SEQ ID NO 15
<211> LENGTH: 22
<212> TYPE: PRT
<213> ORGANISM: Mucor circinelloides CP99001

<400> SEQUENCE: 15

Ala Ser Cys Ser Ser Val Tyr Gly Gln Cys Gly Gly Ile Gly Trp Ser
1               5                   10                  15

Gly Pro Thr Cys Cys Glu
            20

<210> SEQ ID NO 16
<211> LENGTH: 23
<212> TYPE: PRT
<213> ORGANISM: Phycomyces nitens CP99002

<400> SEQUENCE: 16

Ala Glu Cys Ser Gln Gly Tyr Gly Gln Cys Gly Gly Lys Met Trp Thr
1               5                   10                  15

Gly Pro Thr Cys Cys Thr Ser
            20

<210> SEQ ID NO 17
<211> LENGTH: 39
<212> TYPE: PRT
<213> ORGANISM: Artificial Sequence
<220> FEATURE:
```

```
<223> OTHER INFORMATION: Consensus amino acid sequence found in
      cellulose binding domains of the family 45 endoglucanases
<220> FEATURE:
<221> NAME/KEY: MISC_FEATURE
<222> LOCATION: (1)..(6)
<223> OTHER INFORMATION: any amino acid
<220> FEATURE:
<221> NAME/KEY: MISC_FEATURE
<222> LOCATION: (11)..(14)
<223> OTHER INFORMATION: any amino acid
<220> FEATURE:
<221> NAME/KEY: MISC_FEATURE
<222> LOCATION: (16)..(18)
<223> OTHER INFORMATION: any amino acid
<220> FEATURE:
<221> NAME/KEY: MISC_FEATURE
<222> LOCATION: (20)..(25)
<223> OTHER INFORMATION: any amino acid
<220> FEATURE:
<221> NAME/KEY: MISC_FEATURE
<222> LOCATION: (27)..(31)
<223> OTHER INFORMATION: any amino acid
<220> FEATURE:
<221> NAME/KEY: MISC_FEATURE
<222> LOCATION: (33)..(34)
<223> OTHER INFORMATION: any amino acid
<220> FEATURE:
<221> NAME/KEY: MISC_FEATURE
<222> LOCATION: (36)
<223> OTHER INFORMATION: any amino acid
<220> FEATURE:
<221> NAME/KEY: MISC_FEATURE
<222> LOCATION: (39)
<223> OTHER INFORMATION: any amino acid

<400> SEQUENCE: 17

Xaa Xaa Xaa Xaa Xaa Xaa Gln Cys Gly Gly Xaa Xaa Xaa Xaa Gly Xaa
1               5                   10                  15

Xaa Xaa Cys Xaa Xaa Xaa Xaa Xaa Cys Xaa Xaa Xaa Xaa Xaa Xaa Asn
            20                  25                  30

Xaa Xaa Tyr Xaa Gln Cys Xaa
            35

<210> SEQ ID NO 18
<211> LENGTH: 1257
<212> TYPE: DNA
<213> ORGANISM: Humicola insolens
<220> FEATURE:
<221> NAME/KEY: intron
<222> LOCATION: (453)..(509)

<400> SEQUENCE: 18
aatgacgggg caacctcccg cccgggccca actcttgggt ttggtttgac aggccgtctg      60
tctcttgcgt cctcttacta cgcctgcctg gaccctacgt ctcaactccg attcaagatg     120
cgttcctccc ctctcctccg ctccgccgtt gtggccgccc tgccggtgtt ggcccttgcc     180
gctgatggca gtccacccg ctactgggac tgctgcaagc cttcgtgcgg ctgggccaag     240
aaggctcccg tgaaccagcc tgtcttctcc tgcaacgcca acttccagcg tctcactgac     300
ttcgacgcca gtccggctg cgagccgggc ggtgtcgcct actcgtgcgc cgaccagacc     360
ccatgggctg tgaacgacga cttcgcgttc ggttttgctg ccacctctat tgccggcagc     420
aatgaggcgg gctggtgctg cgcctgctac gagtaagctt tggtcgcgtg tgtaacactg     480
tgcaggcata gcactaacca cctcccaggc tcaccttcac atccggtcct gttgctggca     540
agaagatggt cgtccagtcc accagcactg cggtgatct tggcagcaac cacttcgatc     600
tcaacatccc cggcggcggc gtcggcatct tcgacggatg cactccccag ttcggcggtc     660
```

| | |
|---|---:|
| tgcccggcca gcgctacggc ggcatctcgt cccgcaacga gtgcgatcgg ttccccgacg | 720 |
| ccctcaagcc cggctgctac tggcgcttcg actggttcaa gaacgccgac aacccgagct | 780 |
| tcagcttccg tcaggtccaa tgcccagccg agctcgtcgc tcgcaccgga tgccgccgca | 840 |
| acgacgacgg caacttccct gccgtccaga tcccctccag cagcaccagc tctccggtcg | 900 |
| gccagcctac cagtaccagc accacctcca cctccaccac ctcgagcccg cccgtccagc | 960 |
| ctacgactcc cagcggctgc actgctgaga ggtgggctca gtgcggcggc aatggctgga | 1020 |
| gcggctgcac cacctgcgtc gctggcagca cctgcacgaa gattaatgac tggtaccatc | 1080 |
| agtgcctgta aacgcagggc agcctgagaa ccttactggt gcgcaacga aatgacactc | 1140 |
| ccaatcactg tattagttct tgtacataat ttcgtcatcc ctccagggat tgtcacatat | 1200 |
| atgcaatgat gaatactgaa cacaaacctg gccgcttgaa ctggccgaag gaatgcc | 1257 |

<210> SEQ ID NO 19
<211> LENGTH: 1720
<212> TYPE: DNA
<213> ORGANISM: Trichoderma viride
<220> FEATURE:
<221> NAME/KEY: intron
<222> LOCATION: (500)..(682)

<400> SEQUENCE: 19

| | |
|---|---:|
| ggtgtgtcat ttctcctcaa catactgcct ttcaacaact ttcgcctcct ccctggcctg | 60 |
| atatcccaat atcagttttt cccaaagtag caagtcatca gtaaatctgc tcatctatca | 120 |
| ttaatcagtg cccatagtgt ctgtctgttg attgcctccc gccatacacg atgaacagga | 180 |
| ccatggctcc attgctgctt gcagcgtcga tactcttcgg gggcgctgct gcacaacaga | 240 |
| ctgtctgggg acagtgtgga ggtattggtt ggagcggacc tacgagttgt gctcctggat | 300 |
| cagcttgttc tactctcaat ccttattatg cgcaatgcat tccgggggcc actagtatca | 360 |
| ccacctcgac ccgaccccccc tcgggtccaa ccaccaccac cagagccacc tcaacgacct | 420 |
| catctccgcc accgaccagc tctggagttc gatttgctgg cgttaacatc gcgggctttg | 480 |
| acttcggatg taccacagag tatgtcttca tgttgcatag tgttgctggc tgagtattct | 540 |
| gggcggatga tttatagctg tgcgggctgc aaaacaccgc cggtctgcca ctatcaaggc | 600 |
| atagttgata ggcggcggtg ttttcttcaa tcccctgatt acactctcaa gaatctagtg | 660 |
| gctgatggat gtatgattac agtggcactt gcgttacatc gaaggtttat cctccgttga | 720 |
| agaacttcac tggggcaaac aactacccgg acggtatcgg ccagatgcag cacttcgtca | 780 |
| acgatgatgg gatgactatt ttccgcctac ccgtcggatg gcagtacctc gtaaacaaca | 840 |
| atctgggtgg aactctcgat tccaccagta tctcgaagta tgatcagctc gttcaggggt | 900 |
| gcctgtctct cggtgtatac tgcatcatcg acatccacaa ttatgctcga tggaacggtg | 960 |
| gaatcattgg ccagggaggc cctacaaatg cccagtttac cagtctttgg tcgcagttgg | 1020 |
| catcgaagta cgcgtctcag tcgagggtgt ggttcggaat aatgaatgag ccccacgacg | 1080 |
| tgaacatcaa cacttgggct gccacggttc aagaggtcgt cactgcaatc cgcaacgccg | 1140 |
| gtgctacgtc gcaatacatt tctctgcctg gaaatgatta tcaatctgcg gcagcttta | 1200 |
| tttccgatgg cagtgcagcc gccctgtctc aggtaacgaa ccctgatgga tcaacaacga | 1260 |
| atctaatctt cgatgtccac aagtacttag actcggacaa ctccggtact cacgccgaat | 1320 |
| gcactacaaa caacatcgac ggcgcctttg ctcctctcgc cacttggctt cgacagaaca | 1380 |
| accgccaggc tattctgacg gaaaccggcg gtggcaatgt tcagtcctgc atccaagatt | 1440 |

```
tgtgccaaca gatccagtac ctcaaccaga actcagatgt ctatcttggc tatgctggct   1500
ggggtgccgg ttcatttgat agcacttata ttctgacgga aacgcctact ggaagcggta   1560
actcgtggac ggacacatcc ctagttagct cgtgtctcgc caggaagtaa caccgaggtc   1620
gattgcagga gccttgtcaa tagcgatttc atcttgctgt acataattct tactctctga   1680
agccgcttgt tctgggtatg tgtcttgaca ggtttctaga                         1720
```

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 20
caccacgcgc tactgggact                                               20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 21
ggatcctgcg tttacttgc                                                19

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 22
ggatcctggg acaagatg                                                 18

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence:Primer

<400> SEQUENCE: 23
gcacgacggc ttgcagc                                                  17

<210> SEQ ID NO 24
<211> LENGTH: 228
<212> TYPE: PRT
<213> ORGANISM: Artificial Sequence
<220> FEATURE:
<223> OTHER INFORMATION: Description of Artificial Sequence:Recombinant
      protein

<400> SEQUENCE: 24

Met Gln Leu Pro Leu Thr Thr Leu Leu Thr Leu Leu Pro Ala Leu Ala
1               5                   10                  15

Ala Ala Gln Ser Gly Ser Gly Arg Thr Thr Arg Tyr Trp Asp Cys Cys
                20                  25                  30

Lys Pro Ser Cys Ser Trp Pro Gly Lys Ala Asn Val Ser Ser Pro Val
            35                  40                  45

Lys Ser Cys Asn Lys Asp Gly Val Thr Ala Leu Ser Asp Ser Asn Ala
```

-continued

```
                50                  55                  60
Gln Ser Gly Cys Asn Gly Gly Asn Ser Tyr Met Cys Asn Asp Asn Gln
 65                  70                  75                  80

Pro Trp Ala Val Asn Asp Asn Leu Ala Tyr Gly Phe Ala Ala Ala
                 85                  90                  95

Ile Ser Gly Gly Gly Glu Ser Arg Trp Cys Ser Cys Phe Glu Leu
                100                 105                 110

Thr Phe Thr Ser Thr Ser Val Ala Gly Lys Lys Met Val Gln Val
                115                 120                 125

Thr Asn Thr Gly Gly Asp Leu Gly Ser Ser Thr Gly Ala His Phe Asp
130                 135                 140

Leu Gln Met Pro Gly Gly Val Gly Ile Phe Asn Gly Cys Ser Ser
145                 150                 155                 160

Gln Trp Gly Ala Pro Asn Asp Gly Trp Gly Ser Arg Tyr Gly Gly Ile
                165                 170                 175

Ser Ser Ala Ser Asp Cys Ser Ser Leu Pro Ser Ala Leu Gln Ala Gly
                180                 185                 190

Cys Lys Trp Arg Phe Asn Trp Phe Lys Asn Ala Asp Asn Pro Ser Met
                195                 200                 205

Thr Tyr Lys Glu Val Thr Cys Pro Lys Glu Ile Thr Ala Lys Thr Gly
                210                 215                 220

Cys Ser Arg Lys
225

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 25
gcggatcctg ggacaagatg                                                  20

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 26
gcctgcagag cggcggaggc catc                                             24

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 27
gcctgcaggg aaagtacagc gctgt                                            25

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:Primer
```

```
<400> SEQUENCE: 28
gcggatcctg cgtttacttg c                                          21

<210> SEQ ID NO 29
<211> LENGTH: 245
<212> TYPE: PRT
<213> ORGANISM: Artificial Sequence
<220> FEATURE:
<223> OTHER INFORMATION: Description of Artificial Sequence:Recombinant
      protein

<400> SEQUENCE: 29

Met Lys Phe Ile Thr Ile Ala Ser Ser Ala Leu Leu Ala Leu Ala Leu
1               5                   10                  15

Gly Thr Glu Met Ala Ser Ala Ala Leu Gln Gly Lys Tyr Ser Ala Val
            20                  25                  30

Ser Gly Gly Ala Ser Gly Asn Gly Val Thr Thr Arg Tyr Trp Asp Cys
        35                  40                  45

Cys Lys Pro Ser Cys Ser Trp Pro Gly Lys Ala Asn Val Ser Ser Pro
    50                  55                  60

Val Lys Ser Cys Asn Lys Asp Gly Val Thr Ala Leu Ser Asp Ser Asn
65                  70                  75                  80

Ala Gln Ser Gly Cys Asn Gly Gly Asn Ser Tyr Met Cys Asn Asp Asn
                85                  90                  95

Gln Pro Trp Ala Val Asn Asp Asn Leu Ala Tyr Gly Phe Ala Ala Ala
            100                 105                 110

Ala Ile Ser Gly Gly Gly Glu Ser Arg Trp Cys Cys Ser Cys Phe Glu
        115                 120                 125

Leu Thr Phe Thr Ser Thr Ser Val Ala Gly Lys Lys Met Val Val Gln
    130                 135                 140

Val Thr Asn Thr Gly Gly Asp Leu Gly Ser Ser Thr Gly Ala His Phe
145                 150                 155                 160

Asp Leu Gln Met Pro Gly Gly Val Gly Ile Phe Asn Gly Cys Ser
                165                 170                 175

Ser Gln Trp Gly Ala Pro Asn Asp Gly Trp Ser Arg Tyr Gly Gly
            180                 185                 190

Ile Ser Ser Ala Ser Asp Cys Ser Ser Leu Pro Ser Ala Leu Gln Ala
        195                 200                 205

Gly Cys Lys Trp Arg Phe Asn Trp Phe Lys Asn Ala Asp Asn Pro Ser
    210                 215                 220

Met Thr Tyr Lys Glu Val Thr Cys Pro Lys Glu Ile Thr Ala Lys Thr
225                 230                 235                 240

Gly Cys Ser Arg Lys
                245

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence:N-terminus
      sequence of recombinant protein

<400> SEQUENCE: 30

Gln Ser Gly Ser Gly Arg Thr
1               5

<210> SEQ ID NO 31
```

```
<211> LENGTH: 7
<212> TYPE: PRT
<213> ORGANISM: Artificial Sequence
<220> FEATURE:
<223> OTHER INFORMATION: Description of Artificial Sequence:N-terminus
      sequence of recombinant protein

<400> SEQUENCE: 31

Lys Tyr Ser Ala Val Ser Gly
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:N-terminus
      sequence of recombinant protein

<400> SEQUENCE: 32

Ala Val Ser Gly Gly Ala Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence:N-terminus
      sequence of recombinant protein

<400> SEQUENCE: 33

Ser Ala Val Ser Gly Gly Ala
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence:N-terminus
      sequence of recombinant protein

<400> SEQUENCE: 34

Gly Gly Ala Ser Gly Asn Gly
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence:N-terminus
      sequence of recombinant protein

<400> SEQUENCE: 35

Ala Glu Cys Ser Lys Leu Tyr
1               5

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 36
taytgggayt gytgyaarcc                                              20
```

-continued

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (9)
<223> OTHER INFORMATION: i

<400> SEQUENCE: 37
tcngcrttna rraaccartc                                                     20

<210> SEQ ID NO 38
<211> LENGTH: 223
<212> TYPE: PRT
<213> ORGANISM: Humicola insolens

<400> SEQUENCE: 38

```
Met Gln Leu Pro Leu Thr Thr Leu Leu Thr Leu Leu Pro Ala Leu Ala
1               5                   10                  15

Ala Ala Gln Ser Gly Ser Gly Arg Thr Thr Arg Tyr Trp Asp Cys Cys
                20                  25                  30

Lys Pro Ser Cys Ala Trp Pro Gly Lys Gly Pro Ala Pro Val Arg Thr
            35                  40                  45

Cys Asp Arg Trp Asp Asn Pro Leu Phe Asp Gly Gly Asn Thr Arg Ser
        50                  55                  60

Gly Cys Asp Ala Gly Gly Ala Tyr Met Cys Ser Asp Gln Ser Pro
65                  70                  75                  80

Trp Ala Val Ser Asp Leu Ala Tyr Gly Trp Ala Ala Val Asn Ile
                85                  90                  95

Ala Gly Ser Asn Glu Arg Gln Trp Cys Cys Ala Cys Tyr Glu Leu Thr
                100                 105                 110

Phe Thr Ser Gly Pro Val Ala Gly Lys Arg Met Ile Val Gln Ala Ser
            115                 120                 125

Asn Thr Gly Gly Asp Leu Gly Asn Asn His Phe Asp Ile Ala Met Pro
    130                 135                 140

Gly Gly Gly Val Gly Ile Phe Asn Ala Cys Thr Asp Gln Tyr Gly Ala
145                 150                 155                 160

Pro Pro Asn Gly Trp Gly Gln Arg Tyr Gly Gly Ile Ser Gln Arg His
                165                 170                 175

Glu Cys Asp Ala Phe Pro Glu Lys Leu Lys Pro Gly Cys Tyr Trp Arg
                180                 185                 190

Phe Asp Trp Phe Leu Asn Ala Asp Asn Pro Ser Val Asn Trp Arg Gln
            195                 200                 205

Val Ser Cys Pro Ala Glu Ile Val Ala Lys Ser Gly Cys Ser Arg
    210                 215                 220
```

<210> SEQ ID NO 39
<211> LENGTH: 672
<212> TYPE: DNA
<213> ORGANISM: Humicola insolens

<400> SEQUENCE: 39

```
atgcagctcc ccctgaccac gctcctcacc ctcctccccg ccctcgcggc ggcccagtcc      60
ggcagcggcc gcaccacgcg ctactgggac tgctgcaagc cgtcgtgcgc gtggcccggc     120
aagggcccgg cgcccgtgcg gacgtgcgac cggtgggaca acccgctgtt cgacggcggc     180
aacacgcgca gcgggtgcga cgcgggcggc ggcgcctaca tgtgctcgga ccagagcccg     240
tgggcggtca gcgacgacct ggcgtacggc tgggcggccg tcaacattgc cggctccaac     300
gagaggcagt ggtgctgcgc ctgctacgag ctgaccttca ccagcgggcc ggtggcgggc     360
aagaggatga ttgtgcaggc gagcaacacg ggaggcgatt ggggaacaa ccactttgat      420 attgctatgc ccggcggtgg cgtcggtatc ttcaacgcct gcaccgacca gtacggcgcg     480
ccccccaacg gctggggcca cgctacggc ggcatcagcc aacgccacga gtgcgacgcc      540
ttccccgaga agctcaagcc cggctgctac tggcgctttg actggttcct caacgccgac     600
aacccgagcg tcaactggcg gcaggtcagc tgcccggccg agattgtggc caagagcggc     660
tgctcgcgtt aa                                                         672
```

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence:Primer
<400> SEQUENCE: 40

```
ggggatcctg ggacaagatg cagctccccc tgaccacg                              38
```

<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence:Primer
<400> SEQUENCE: 41

```
ggggatcctg catttaacgc gagcagccgc tcttggcc                              38
```

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:Primer
<400> SEQUENCE: 42

```
gactgctgca agccgtcgtg c                                                21
```

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:Primer
<400> SEQUENCE: 43

```
gttgcacatg taggagttgc                                                  20
```

ZYGOMYCETES-DERIVED ENDOGLUCANASE ENZYME LACKING CELLULOSE-BINDING DOMAIN

TECHNICAL FIELD

The present invention relates to an endoglucanase enzyme, the cellulose-binding domain of which has been deleted, with enhanced effects in the treatment of cellulose-containing fabrics and with applications regarding detergents or paper pulp, a method for producing the same, and a cellulase preparation with enhanced effects.

BACKGROUND ART

Treatment of cellulose-containing fabrics with cellulase is carried out to provide the fabrics with desired properties. For example, treatment with cellulase is carried out in the fabric industry in order to improve the feel and appearance of cellulose-containing fabrics or to give colored cellulose-containing fabrics an appearance of "stone-washed" material, i.e., partial color change (European Patent No. 307,564).

Colored cellulose-containing fabrics are known to become fuzzy after repeated washings and to lose their vividness. Incorporation of cellulase into a detergent can remove fuzz and make the color of fabrics vivid, i.e., clarify the color (European Patent No. 220,016). Thus, detergents containing cellulase are commercially available mainly in Europe and America.

In the aforementioned application, cellulases derived from *Trichoderma* or *Humicola* (both are wood-rotting fungi) are mainly used. Recently used cellulase preparations are produced by isolating endoglucanases, which are highly active in fabric treatment, from these cellulase components and enhancing their effects with genetic engineering in order to improve commercial efficiency. Examples of these highly active endoglucanases include: *Humicola insolens*-derived EG V (WO 91/17243) and NCE4 (WO 98/03640) that strongly act on cotton fabrics; and *Rhizopus oryzae*-derived RCE I, RCE II, and RCE III, *Mucor circinelloides*-derived MCE I and MCE II, and *Phycomyces nitens*-derived PCE I (WO 00/24879) that strongly act on lyocell fabrics.

Among endoglucanases used in the aforementioned applications, EG V (WO 91/17243), NCE4 (WO 98/03640), and RCE I, RCE II, RCE III, MCE I, MCE II, and PCE I (WO 00/24879) are presumed to belong to the same family (family 45) because of their amino acid sequences, and these enzymes have common structural properties. Specifically, each of these endoglucanases comprises a cellulose-binding domain for binding to cellulose as its substrate (hereinafter referred to as "CBD"), a catalytic active domain as an active center (hereinafter referred to as "CAD"), and a linker domain with a high hydrophilic amino acid residue content for linking these two domains.

EG V, an endoglucanase belonging to family 45, was studied using an enzyme, the CBD domain of which had been deleted (JP Patent Publication (PCT Translation) No. 9-500667, Enzyme and Microbial Technology, 27 (2000), 325-329). However, no improvement has been reported regarding the activity of endoglucanase for removing fuzz from cellulose fabrics through the deletion of the cellulose-binding domain (CBD). There are still many unclarified matters concerning the role of the cellulose-binding domain of endoglucanase in the exhibition of endoglucanase activity, and research thereof is limited to cellulase derived from a specific fungus, namely, *Trichoderma* (Kiovula, A. et al., *Trichoderma Gliocladium*, 2, (1998), 3-23). There has been no detailed research on the cellulose-binding domain of the *Zygomycetes*-derived endoglucanase.

Up to the present, several contrivances have been made in order to improve the effect or performance of cellulase in the above applications. For example, mutation was applied to an enzyme for improvement thereof, or culture conditions were modified in order to improve the productivity of the enzyme. Due to the high cost of cellulase to be used, however, the effect of cellulase should be further improved in order to provide a cellulase preparation that is worth using at an industrially practical level. Recently used cellulase preparations are produced by reinforcing only endoglucanase, which is highly active in fabric treatment, with genetic engineering in order to improve commercial efficiency. Accordingly, it is desirable to further improve the activity of such highly active cellulase.

DISCLOSURE OF THE INVENTION

An object of the present invention is to provide an endoglucanase with improved activity, a cellulase preparation comprising the same, and various methods for treating cellulose-containing fabrics using the same.

The present inventors have conducted concentrated studies on the *Zygomycetes*-derived endoglucanase concerning the role of a cellulose-binding domain when acting on cellulose-containing fabrics. As a result, they have found that an endoglucanase lacking the cellulose-binding domain has much higher activity of removing fuzz from cotton, lyocell, or the like compared to an endoglucanase having a cellulose-binding domain. This led to the completion of the present invention.

Specifically, the present invention relates to a *Zygomycetes*-derived endoglucanase that has enhanced effects for removing fuzz from cellulose-containing fabrics (e.g., an enzyme comprising amino acid sequences of RCE I, RCE II, RCE III, MCE I, MCE II, and PCE I, which attained enhanced effects of removing fuzz from cellulose-containing fabrics through the deletion of the cellulose-binding domain, and exhibiting endoglucanase activity, a modified protein thereof exhibiting endoglucanase activity, or a homologue of the protein or the modified protein) and a cellulase preparation comprising such endoglucanase. The present invention also relates to an endoglucanase that was produced in a host cell transformed with a gene encoding such an endoglucanase, and further relates to a method for treating cellulose-containing fabrics using the endoglucanase, which attained improved activity through the deletion of the cellulose-binding domain, or the cellulase preparation.

More specifically, the present invention includes the following.

(1) A protein that is a *Zygomycetes*-derived endoglucanase lacking the cellulose-binding domain and exhibits endoglucanase activity.

(2) A protein that is a *Zygomycetes*-derived endoglucanase belonging to family 45 lacking the cellulose-binding domain and exhibits endoglucanase activity.

(3) The protein according to (1) or (2), wherein the *Zygomycetes* are microorganisms selected from the group consisting of those belonging to *Rhizopus, Mucor,* and *Phycoinyces*.

(4) The protein according to (3), wherein the *Zygomycetes* are microorganisms belonging to *Rhizopus*.

(5) A protein comprising an amino acid sequence as shown in SEQ ID NO: 1, 3, 5, 7, 9, or 11, wherein the cellulose-binding domain has been deleted therefrom, and exhibiting endoglucanase activity, a modified protein thereof exhibiting endoglucanase activity, or a homologue of the protein or the modified protein exhibiting endoglucanase activity.

(6) A protein comprising an amino acid sequence as shown in SEQ ID NO: 1, 3, 5, 7, 9, or 11, wherein the cellulose-binding domain has been deleted therefrom, and exhibiting endoglucanase activity.

(7) A gene encoding the protein, modified protein thereof, or homologue of the protein or the modified protein according to any one of (1) to (6).

(8) An expression vector comprising the gene according to (7).

(9) A host cell transformed with the expression vector according to (8).

(10) The host cell according to (9), which is a filamentous fungus.

(11) The host cell according to (10), which is a microorganism belonging to *Humicola*.

(12) A method for producing a protein comprising steps of culturing the host cell according to any one of (9) to (11) and collecting from the host cell obtained by the step of culturing or its culture product the protein, modified protein thereof, or homologue of the protein or the modified protein according to any one of (1) to (6).

(13) A protein produced by the method according to (12).

(14) A cellulase preparation comprising the protein, modified protein thereof, or homologue of the protein or the modified protein according to any one of (1) to (6) and (13).

(15) A method for treating cellulose-containing fabrics comprising a step of bringing cellulose-containing fabrics into contact with the protein, modified protein thereof, or homologue of the protein or the modified protein according to any one of (1) to (6) and (13) or the cellulase preparation according to (14).

(16) A method for reducing the rate at which cellulose-containing fabrics become fuzzy or reducing fuzzing in cellulose-containing fabrics comprising a step of bringing cellulose-containing fabrics into contact with the protein, modified protein thereof, or homologue of the protein or the modified protein according to any one of (1) to (6) and (13) or the cellulase preparation according to (14).

(17) A method of weight loss treatment of cellulose-containing fabrics to improve the feel and appearance thereof comprising a step of bringing cellulose-containing fabrics into contact with the protein, modified protein thereof, or homologue of the protein or the modified protein according to any one of (1) to (6) and (13) or the cellulase preparation according to (14).

(18) A method of color clarification of colored cellulose-containing fabrics comprising a step of treating colored cellulose-containing fabrics with the protein, modified protein thereof, or homologue of the protein or the modified protein according to any one of (1) to (6) and (13) or the cellulase preparation according to (14).

(19) A method of providing colored cellulose-containing fabrics with partial color change comprising a step of treating colored cellulose-containing fabrics with the protein, modified protein thereof, or homologue of the protein or the modified protein according to any one of (1) to (6) and (13) or the cellulase preparation according to (14).

(20) A method for reducing the rate at which cellulose-containing fabrics become stiff or reducing stiffness in cellulose-containing fabrics comprising a step of treating cellulose-containing fabrics with the protein, modified protein thereof, or homologue of the protein or the modified protein according to any one of (1) to (6) and (13) or the cellulase preparation according to (14).

(21) The method according to any one of (15) to (20), wherein fabrics are treated through soaking, washing, or rinsing thereof.

(22) An additive to detergent comprising the protein, modified protein thereof, or homologue of the protein or the modified protein according to any one of (1) to (6) and (13) or the cellulase preparation according to (14) in a non-dusting granular form or a stabilized liquid form.

(23) A detergent composition comprising the protein, modified protein thereof, or homologue of the protein or the modified protein according to any one of (1) to (6) and (13) or the cellulase preparation according to (14).

(24) A method of deinking waste paper using a deinking aagent wherein the protein, modified protein thereof, or homologue of the protein or the modified protein according to any one of (1) to (6) and (13) or the cellulase preparation according to (14) is used in a step of deinking waste paper.

(25) A method for improving drainage of paper pulp comprising a step of treating paper pulp with the protein, modified protein thereof, or homologue of the protein or the modified protein according to any one of (1) to (6) and (13) or the cellulase preparation according to (14).

(26) A method for improving digestibility of animal feeds comprising a step of treating animal feeds with the protein, modified protein thereof, or homologue of the protein or the modified protein according to any one of (1) to (6) and (13) or the cellulase preparation according to (14).

1. Endoglucanase Lacking Cellulose-Binding Domain

The present invention relates to a protein that is a *Zygomycetes*-derived endoglucanase lacking the cellulose-binding domain and exhibits endoglucanase activity.

In this description, "*Zygomycetes*" refer to microorganisms belonging to Zygomycota, i.e., fungi that generate zygospores through gametangial copulation upon gametogony. The *Zygomycota* includes *Zygomycetes* and *Trichomycetes*. The *Zygomycetes* used in the present invention are not particularly limited. Microorganisms belonging to the *Zygomycetes* are preferable, those belonging to the *Mucorales* are more preferable, those belonging to *Rhizopus, Mucor,* or *Phycomyces* are still more preferable, and those belonging to the *Rhizopus* are the most preferable.

In this description, "endoglucanase activity" refers to CMCase activity. Further, "CMCase activity" refers to an activity for hydrolyzing carboxymethylcellulose (CMC, Tokyo Kasei Kogyo, Japan), and one unit is defined as the amount of an enzyme which produces reducing sugars corresponding to 1 µmol of glucose per minute by measuring amounts of the reducing sugars released after incubation of a test protein with a CMC solution for a given period of time.

Endoglucanase activity can be determined by, for example, a procedure as described below. At the outset, 0.5 ml of a solution containing a test protein is added to 0.5 ml of 50 mM acetic acid-sodium acetate buffer solution (pH 6.0) with 2% CMC dissolved therein, and the mixture is subjected to incubation at 50° C. for 30 minutes. Subsequently, the concentration of the reducing sugars produced in the resulting reaction solution is quantified by the 3,5-dinitrosalicylic acid (DNS) method. Specifically, 3.0 ml of a DNS reagent is added to 1.0 ml of the reaction solution 30 minutes after the reaction, and the mixture is subjected to incubation in a boiling water bath for 5 minutes. Thereafter, the incubation product is diluted with 8.0 ml of distilled water, and the absorbance at 540 nm is measured. A calibration curve is prepared using a gradually diluted glucose solution, and the amount of the reducing sugars produced in the enzyme reaction solution is determined. Activity is determined using an amount of the enzyme that produces reducing sugars corresponding to 1 μmol glucose per minute as one unit. This DNS reagent can be prepared in accordance with publication such as Seibutsu Kagaku Jikkenhou 1- Kangentou no Teiryouhou (Biochemical Experimentation 1- The method for quantifying reducing sugar) (p. 19-20, Sakuzo Fukui, Center for Academic Publications Japan), and can be prepared in the manner described below. At the outset, 880 ml of 1% 3,5-dinitrosalicylic acid solution and 255 g of Rochelle salt are added to 300 ml of an aqueous solution of 4.5% sodium hydroxide (solution A). Separately, 10 g of crystalline phenol is added to 22 ml of an aqueous solution of 10% sodium hydroxide, and water is further added and dissolved in the mixture to bring the amount thereof to 100 ml (solution B). Sodium bicarbonate (6.9 g) is added to 69 ml of solution B and dissolved therein, solution A is poured therein, and the mixture is stirred and mixed until the Rochelle salt is thoroughly dissolved. The mixture is allowed to stand for 2 days and then filtered.

The term "endoglucanase" used herein refers to an enzyme exhibiting endoglucanase activity, i.e., endo-1,4-β-glucanase (EC 3. 2. 1. 4). This enzyme hydrolyzes the β-1,4-glucopyranosyl bonds of β-1,4-glucan.

Endoglucanases are classified into several families based on information such as their amino acid sequences. The endoglucanase according to the present invention may belong to any family, and it preferably belongs to family 45. The endoglucanase "belonging to family 45" refers to those types having a consensus sequence, (Ser, Thr, or Ala)-Thr-Arg-Tyr-(Trp, Tyr, or Phe)-Asp-Xaa-Xaa-Xaa-Xaa-Xaa-(Cys or Ala) SEQ ID NO: 44, in the catalytic active domain (CAD). *Humicola insolens*-derived EG V (JP Patent Publication (PCT Translation) No. 5-509223), NCE4 (WO 98/03640), and the like also belong to family 45.

A protein of endoglucanase belonging to family 45 is comprised a catalytic active domain (CAD), a cellulose-binding domain (CBD), and a linker domain for binding based on function. The cellulose-binding domain (CBD) is known to exist as a domain linking to cellulose as its name suggests, and the conservation of the following consensus sequence is confirmed as a feature of the sequence (Hoffren, A.-M. et al., Protein Engineering 8: 443-450, 1995).

Although there is no definite recognition sequence for the linker domain, the sequence is rich in hydrophilic amino acid residues such as Ser or Thr, and its length varies depending on types of endoglucanases.

Examples of the *Zygomycetes*-derived endoglucanase according to the present invention include enzymes exhibiting endoglucanase activity derived from *Rhizopus, Phycomuyces,* or *Mucor* described in WO 00/24879, i.e., RCE I (SEQ ID NO: 1), RCE II (SEQ ID NO: 3), RCE III (SEQ ID NO: 5), MCE I (SEQ ID NO: 7), MCE II (SEQ ID NO: 9), and PCE I (SEQ ID NO: 11). Locations of each of the domains in the amino acid sequence of these enzymes are as shown in Table 1 below.

TABLE 1

|  | CBD | A portion in linker domain | CAD |
|---|---|---|---|
| SEQ ID NO: 1 | 3 to 38 | 99 to 108 | 109 to 315 |
| SEQ ID NO: 3 | 3 to 38 | 127 to 136 | 137 to 343 |
|  | 50 to 85 |  |  |
| SEQ ID NO: 5 | 3 to 40 | 122 to 131 | 132 to 337 |
| SEQ ID NO: 7 | 3 to 40 | 104 to 113 | 114 to 316 |
| SEQ ID NO: 9 | 3 to 40 | 153 to 162 | 163 to 365 |
|  | 52 to 89 |  |  |
| SEQ ID NO: 11 | 3 to 40 | 115 to 124 | 125 to 327 |

Amino acid sequences at the N-terminuses of RCE I, MCE I, and PCE I are respectively identified as shown in SEQ ID Nos: 14, 15, and 16 (WO 00/24879).

The protein according to the present invention should not comprise a cellulose-binding domain in the aforementioned endoglucanase. As long as the protein has endoglucanase activity, there is no particular limitation on the structure of other domains. Accordingly, the protein of the present invention may or may not comprise a linker domain. The protein may alternatively comprise a portion of a linker domain, and it is preferable if the protein retains a fragment of a linker domain comprising about 10 amino acid residues.

The other aspect of the present invention relates to a protein comprising any of the amino acid sequences as shown in SEQ ID NO: 1 (RCE 1), SEQ ID NO: 3 (RCE II), SEQ ID NO: 5

```
                CBD consensus sequence:

1                              10
Xaa Xaa Xaa Xaa Xaa Xaa Gln Cys Gly Gly Xaa Xaa Xaa Xaa   (SEQ ID NO: 17)

20
Gly Xaa Xaa Xaa Cys Xaa Xaa Xaa Xaa Xaa Xaa Cys Xaa Xaa

30
Xaa Xaa Xaa Asn Xaa Xaa Tyr Xaa Gln Cys Xaa
```

In this sequence, Xaa is independently any amino acid; and Xaas at positions 20, 21, 22, 23, 24, 30 and 31 may be independently absent. Other Xaas are always present and are independently any amino acids. Amino acids other than Xaa are expressed in three-letter abbreviations. CBD is linked to either the N-terminal side or C terminal side of CAD through a linker domain. Also reported is *Humicola insolens*-derived NCE5 (amino acid sequence: SEQ ID NO: 38, cDNA sequence: SEQ ID NO. 39) such as a family 45 endoglucanase that does not originally have CBD.

(RCE III), SEQ ID NO: 7 (MCE I), SEQ ID NO: 9 (MCE II), or SEQ ID NO: 11 (PCE I), wherein the cellulose-binding domain has been deleted therefrom, and exhibiting endoglucanase activity. The present invention further relates to a modified protein and a homologue of such protein exhibiting endoglucanase activity.

In this description, the term "modified protein" refers to a protein that comprises an amino acid sequence having modification such as addition, insertion, diminution, deletion, or substitution of one or several amino acids in the amino acid sequence of RCE I, RCE II, RCE III, MCE I, MCE II, or PCE I, which lacks the cellulose-binding domain. The number of the amino acids to be involved with such modification is not particularly limited as long as the modified protein has endoglucanase activity. The number thereof is preferably 1 to about 50, more preferably 1 to about 30, and still more preferably 1 to 9.

The term "homologue" used herein refers to a polypeptide having an amino acid sequence coded by a gene (nucleotide sequence) that hybridizes under stringent conditions with DNA having any nucleotide sequence as shown in SEQ ID NO: 2 or 13 (RCE I), SEQ ID NO: 4 (RCE II), SEQ ID NO: 6 (RCE III), SEQ ID NO: 8 (MCE I), SEQ ID NO: 10 (MCE II), or SEQ ID NO: 12 (PCE I), wherein a portion encoding a cellulose-binding domain has been removed and also having endoglucanase activity. The term "stringent conditions" refers to conditions under which, while a probe that comprises the nucleotide sequence encoding a part or all of the amino acid sequences of RCE I, RCE II, RCE III, MCE I, MCE II, and PCE I lacking the cellulose-binding domain or an amino acid sequence of its modified protein hybridizes with a gene encoding a homologue, this probe is controlled to such an extent that it does not hybridize with the endoglucanase NCE4 gene (SEQ ID NO: 18) according to WO 98/03640 or the endoglucanase SCE3 gene (SEQ ID NO: 19) according to WO 98/54332 (wherein the amount of DNA used is equal to that of the gene encoding the NCE4 gene, SCE3 gene, or a homologue). A specific example of "stringent conditions" is as follows. A labeled probe having a full length DNA sequence encoding amino acid sequences such as RCE I, which lacks the cellulose-binding domain, is used. In accordance with the method of the ECL Direct DNA/RNA Labeling Detection System (Amersham), prehybridization is carried out at 42° C. for 1 hour, the probe is added, and hybridization is then carried out at 42° C. for 15 hours. Thereafter, 0.5×SSC (1×SSC; 15 mM trisodium citrate, 150 mM sodium chloride) comprising 0.4% SDS and 6M urea is used to perform washing twice at 42° C. for 20 minutes. Subsequently, 5×SSC is used to perform washing twice at room temperature (about 25° C.) for 10 minutes.

Examples of such modified proteins or homologue include a protein having an amino acid sequence that is preferably at least 70%, more preferably at least 80%, still more preferably at least 90%, even more preferably at least 95%, and most preferably at least 98% homologous to the amino acid sequence of RCE I, RCE II, RCE III, MCE I, MCE II, or PCE I, which lacks the cellulose-binding domain. The numerical values indicating homology may be determined using a program for searching for homology that is known to a person skilled in the art. Preferably, these numerical values are determined using default (initial setting) parameters at FASTA3 (Science, 227, 1435-1441 (1985); Proc. Natl. Acad. Sci. USA, 85, 2444-2448 (1988).

The protein of the present invention does not comprise a cellulose-binding domain. Accordingly, the modified protein and the homologue should not comprise a cellulose-binding domain. This can be confirmed by investigating the amino acid sequence of the object protein and whether or not the consensus sequence (Hoffren, A.-M. et al., Protein Engineering 8: 443-450, 1995; SEQ ID NO: 17) is present therein.

Also, the protein of the present invention has endoglucanase activity. Accordingly, the modified protein and the homologue should also have endoglucanase activity. This can be confirmed by investigating endoglucanase activity of the object protein by the aforementioned method.

The protein of the present invention can be produced as a protein comprising an amino acid sequence that does not comprise a cellulose-binding domain by a method known to a person skilled in the art based on the amino acid sequence of a known endoglucanase derived from Zygomycetes. Examples of such a method include a method that is carried out by decomposing in a linker domain using protease during the culture of Zygomycetes producing endoglucanase to cause deletion of the cellulose-binding domain and a method that is carried out by artificially expressing endoglucanase that does not have a cellulose-binding domain due to genetic engineering techniques. Among the proteins of the present invention, in particular, the modified protein and the homologue can be prepared using DNA encoding their amino acid sequences by a genetic engineering technique that is known to a person skilled in the art.

The protein of the present invention can yield a higher effect than the original endoglucanase having a cellulose-binding domain in fabric treatment or other applications to detergents or paper pulp. Particularly, a much higher effect can be attained in the activity of removing fuzz from reproduced cellulose fabric such as lyocell (per protein weight) and in the activity of removing fuzz from cotton fabric such as knitted cotton (per protein weight). The protein of the present invention is preferably twice or higher, more preferably 2.5 times or higher, and most preferably 3 times or higher in the activity of removing fuzz from reproduced cellulose fabric (such as lyocell) (per protein weight) as a purified endoglucanase having the cellulose-binding domain. Or, the protein is preferably 5 times or higher, more preferably 15 times or higher, and most preferably 20 times or higher in the activity of removing fuzz from cotton fabric such as knitted cotton (per protein weight) as a purified endoglucanase having the cellulose-binding domain.

2. Gene, Expression Vector, Host Cell Transformed with the Expression Vector, and Production of Endoglucanase Lacking the Cellulose-Binding Domain Using the Host Cell The present invention relates to a gene encoding the protein of the present invention, a modified protein thereof, or a homologue of the protein or the modified protein and an expression vector comprising the gene.

The gene of the present invention may be any gene as long as it encodes the protein of the present invention, a modified protein thereof, or a homologue of the protein or the modified protein. Specific details of their nucleotide sequences are not particularly limited. Examples of usable genes in order to express RCE I RCE II, RCE III, MCE I, MCE II, or PCE I, which lacks the cellulose-binding domain, as the protein of the present invention include those comprising nucleotide sequences as shown in SEQ ID NO: 2 (RCE I), SEQ ID NO: 4 (RCE II), SEQ ID NO: 6 (RCE III), SEQ ID NO: 8 (MCE I), SEQ ID NO: 10 (MCE II), or SEQ ID NO: 12 (PCE I).

Specifically, the gene of the present invention comprises an amino acid sequence as shown in SEQ ID NO: 1, 3, 5, 7, 9, or 11, wherein the cellulose-binding domain has been deleted therefrom, and encodes a protein exhibiting endoglucanase activity, a modified protein thereof exhibiting endoglucanase activity, or a homologue of the protein or the modified protein exhibiting endoglucanase activity.

The gene of the present invention comprises DNA as described in the following (a) or (b).
(a) DNA that has a nucleotide sequence as shown in SEQ ID NO: 2 or 13, 4, 6, 8, 10, or 12, wherein a portion encoding a cellulose-binding domain has been deleted therefrom.
(b) DNA that hybridizes under stringent conditions with DNA that has a nucleotide sequence as shown in SEQ ID NO: 2 or 13, 4, 6, 8, 10, or 12, wherein a portion encoding a cellulose-binding domain has been deleted therefrom.

The term "stringent conditions" means the conditions described in the section 1. above.

The nucleotide sequences of the aforementioned genes can be optimized depending on the type of host cell used in the later transformation. These nucleotide sequences can be optimized with respect to, for example, the codon usage in a host cell or the intron recognition sequence in a host cell. The codon usage can be optimized by, for example, modifying nucleotide sequences so as to comprise as many codons used in a host cell at high frequency as possible without changing the amino acid sequence to be coded. This can improve the efficiency of translation from genes into proteins. The intron recognition sequence can be optimized by, for example, modifying nucleotide sequences so as to have no DNA sequence, which could be recognized as an intron in a host cell, or to have as few sequences as possible without changing the amino acid sequence to be coded. This can improve the stability of mRNA that is a transcript of an object gene. The intron recognition sequences vary depending on types of host cells. Examples of intron recognition sequences of filamentous fungi belonging to the Fungi imperfecti include DNA sequences such as GTAGN, GTATN, GTAAN, GTACGN, GTGTN, GCACGN, and GTTCGN ("N" stands for A, T, C, or G in each sequence).

In this description, the term "codon optimized gene" refers to a gene that is obtained by optimizing the codon usage and/or the intron recognition sequence. Preferably, the codon optimized gene is a gene obtained by optimizing the codon usage, and more preferably a gene obtained by optimizing the codon usage and the intron recognition sequence. This codon optimized gene is preferably optimized for the expression in filamentous fungi belonging to the Fungi imperfecti. Examples of such codon optimized genes include a gene which lacks a portion encoding a cellulose-binding domain in the codon optimized endoglucanase RCE I gene (SEQ ID NO; 13) as disclosed in WO 00/24879.

The expression vector of the present invention comprises an object gene (a gene encoding the protein of the present invention, a modified protein thereof, or a homologue of the protein or the modified protein) in a state that is replicable in a host cell and expressible of the protein of the present invention, a modified protein thereof, or a homologue of the protein or the modified protein. This expression vector can be constructed based on a self-replicating vector, i.e., a vector that exists as an extrachromosomal vector and replicates independently of the chromosome, for example, a plasmid. Alternatively, the expression vector may be a vector that is integrated into the genome of the host cell upon introduction thereinto and replicated together with the chromosome into which it has been incorporated. For the construction of the vector of the present invention, conventional procedures and methods used in the field of genetic engineering can be used.

For the expression of the protein of the present invention, a modified protein thereof, or a homologue of the protein or the modified protein upon introduction into the host cell, it is desirable that the expression vector of the invention contains DNA sequences to regulate the expression and gene markers, etc. to select transformants, in addition to the gene encoding the protein of the present invention, a modified protein thereof, or a homologue of the protein or the modified protein. Examples of expression regulatory DNA sequences include promoters, terminators, and DNA sequences encoding signal peptides. The promoters and the terminators are not particularly limited as long as they show transcription activity in the host cell. They may be obtained as DNA sequences, which control the expression of a gene encoding a protein homogeneous or heterogeneous to the host cell. The signal peptides are not particularly limited as long as they contribute to the secretion of protein in the host cell. They may be obtained from DNA sequences derived from a gene encoding a protein homogeneous or heterogeneous to the host cell. The gene markers of the invention can be appropriately selected depending on the method for selecting transformants. For example, genes encoding drug resistance or genes complementing auxotrophy may be used. Each of these DNA sequences and gene markers is operably linked to the expression vector of the present invention.

Further, the present invention relates to a host cell that is transformed with the expression vector. The expression vector introduced into a host cell should be replicable therein. Thus, the host cell that is used herein varies depending on the type of vector used in the production of the expression vector. Alternatively, in accordance with the type of a host cell to be used, an expression vector can be produced so as to be replicable therein. Specifically, in order to obtain a transformant that expresses the protein of the present invention, a modified protein thereof, or a homologue of the protein or the modified protein, a host cell and an expression vector should be adequately combined. Such a combination is referred to as a host-vector system. The host-vector system that is used in the present invention is not particularly limited. Examples thereof include systems using microorganisms such as *Escherichia coli*, Actinomycetes, yeast, and filamentous fungi as host cells, and a system using filamentous fungi is preferred. An expression system for a fusion protein with other protein can be also used.

When filamentous fungi are used as host cells, any type of filamentous fungi can be used, and preferred examples thereof include those belonging to *Humicola, Aspergillus*, or *Trichoderma*. Particularly preferred examples of these filamentous fungi include *Humicola incolens, Aspergillus niger* or *Aspergillus oryzae*, and *Trichoderma viride*.

A host cell can be transformed with the expression vector of the present invention in accordance with conventional methods used in the field of genetic engineering.

The thus obtained transformant (transformed host cell) is cultured in a suitable medium, and the protein of the present invention, a modified protein thereof, or a homologue of the protein or the modified protein can be isolated and obtained from the culture product. Accordingly, another aspect of the present invention relates to a method for producing a protein comprising steps of culturing the host cell of the present invention and collecting the protein of the present invention, a modified protein thereof, or a homologue of the protein or the modified protein from the host cell obtained by the step of culture or a culture product thereof. Culture methods and other conditions for transformants may be substantially the same as those for microorganisms to be used. The transformants can be cultured and the object protein can be then collected by a conventional method of this technical field.

3. Cellulase Preparation

The present invention relates to a cellulase preparation that comprises the protein of the present invention, a modified protein thereof, a homologue of the protein or the modified protein, or a protein produced by the method for producing a protein according to the present invention.

In general, a cellulase preparation is powder, liquid, or the like that comprises, for example, an excipient (e.g., lactose, sodium chloride, or sorbitol), a preservative, or a nonionic surfactant, in addition to a cellulase enzyme. For example, it is formulated as a powdery, particulate, granular, non-dusting granular, or liquid preparation. The cellulase preparation of the present invention comprises, as the cellulase enzyme, the protein of the present invention, a modified protein thereof, a homologue of the protein or the modified protein, or a protein produced by the method for producing a protein of the present invention (hereinafter referred to as "the proteins of the present invention"). Further, the cellulase preparation of the present invention may comprise, in addition to the proteins of the present invention, other cellulase enzymes, for example, cellobiohydrolase, β-glucosidase, or endoglucanase which are not involved in the present invention.

One type of cellulase preparation, a non-dusting granular preparation, may be prepared by a conventional dry granulating method. Specifically, the powdery proteins of the present invention are mixed with one or several of: neutral inorganic salts that do not affect endoglucanase activity represented by sodium sulfate, sodium chloride, or the like; minerals that do not affect endoglucanase activity represented by bentonite, montmorillonite, or the like; or neutral organic substances represented by starch, particulate cellulose, or the like. A powder or fine suspension of one or several nonionic surfactant is then added thereto, followed by thorough mixing or kneading. Depending on the situation, a synthetic polymer represented by polyethylene glycol for binding solid matter or a natural polymer such as starch is suitably added and further kneaded. Thereafter, extrusion granulation is carried out using, for example, Disc Pelleter, and the extruded granules are then shaped into spherical form using the Marumerizer, followed by drying. Thus, non-dusting granules can be produced. The amount of one or several nonionic surfactants to be added is not particularly limited. The amount is preferably 0.1% to 50% by weight, more preferably 0.1% to 30% by weight, and still more preferably 1% to 20% by weight, based on the entire cellulase preparation according to the present invention. Oxygen permeation or water permeation can be regulated by coating the surfaces of granules with a polymer, etc.

In contrast, a liquid formulation can be prepared by incorporating a stabilizer for the endoglucanase enzyme such as a synthetic polymer, a natural polymer, or the like into a solution comprising the proteins of the present invention and adding inorganic salts or synthetic preservatives according to need. In this case, one or several nonionic surfactants can be also incorporated. The amount of one or several nonionic surfactants to be added is not particularly limited. The amount is preferably 0.1% to 50% by weight, more preferably 0.1% to 30% by weight, and still more preferably 1% to 20% by weight, based on the entire cellulase preparation according to the present invention.

4. Application of the Proteins of the Present Invention and the Cellulase Preparation of the Present Invention The present invention relates to a method for treating cellulose-containing fabrics. This method comprises a step of bringing cellulose-containing fabrics into contact with the proteins of the present invention or the cellulase preparation of the present invention. Conditions such as contact temperature or amounts of the proteins or the cellulase preparation can be suitably determined with respect to various other conditions.

The aforementioned method can be used to reduce the rate at which cellulose-containing fabrics become fuzzy or to reduce fuzzing in cellulose-containing fabrics. In this application, the proteins or the cellulase preparation at the protein concentration of 0.001 to 1 mg/l is preferably used at about 30° C. to 60° C.

The aforementioned method can be used in weight loss treatment of cellulose-containing fabrics to improve the feel and appearance thereof. In this application, to improve the feel means to reduce the rate at which the feel is spoiled. In this application, the proteins or the cellulase preparation at the protein concentration of 0.001 to 100 mg/l is preferably used at about 30° C. to 60° C.

The aforementioned method can be used for color clarification of colored cellulose-containing fabrics.

The aforementioned method can be used for providing colored cellulose-containing fabrics with partial color change. In this application, for example, colored cellulose-containing fabrics (e.g., denim) can be provided with an appearance of stone-washed material. In this application, the proteins or the cellulase preparation at the protein concentration of 0.01 to 100 mg/l is preferably used at about 40° C. to 60° C.

The protein concentrations of various endoglucanases were calculated from the peak area at UV 280 nm of respective endoglucanase eluted with a linear gradient from 0% to 80% of acetonitrile concentration in 0.05% TFA (trifluoroacetic acid) at a flow rate of 1.0 ml/min in HPLC analysis using TSK gel TMS-250 column (4.6 mm I.D.×7.5 cm, TOSOH Japan). The standard used was the purified NCE4, which was analyzed in HPLC under the same conditions, the protein concentration of which had been preliminarily measured by a protein assay kit (BioRad Laboratories). The purified NCE4 is purified from a culture product of *Humicola incolens* MN 200-1, which was deposited at the International Patent Organism Depositary of the National Institute of Advanced Industrial Science and Technology (Tsukuba Central 6, 1-1-1 Higashi, Tsukuba, Ibaraki, Japan) under the accession number of FERM BP-5977 (initial deposition: FERM P-15736, date of initial deposition: Jul. 15, 1996), in accordance with the method as described in WO 98/03640. The standard used to measure the protein concentration using the protein assay kit is the Albumin Standard (Bovine serum albumin, fraction V, PIERCE).

The aforementioned method can be used to reduce the rate at which cellulose-containing fabrics become stiff or to reduce stiffness in cellulose-containing fabrics. In this application, cellulose-containing fabrics can be softened.

In the aforementioned applications, cellulose-containing fabrics can be treated through soaking, washing, or rinsing of the fabrics. Specifically, the aforementioned method of the present invention can be carried out by treating cellulose-containing fabrics during washing. On some occasions, however, the treatment of fabrics may be carried out during soaking or rinsing by adding the proteins or the cellulase preparation of the present invention into water where the fabrics are soaked or to be soaked.

The present invention relates to an additive to detergent comprising the proteins or the cellulase preparation of the present invention in a non-dusting granular form or a stabilized liquid form. The present invention further relates to a detergent composition comprising the proteins or the cellulase preparation of the present invention.

This detergent composition may also contain a surfactant (which may be anionic, nonionic, cationic, amphoteric, or zwitterionic surfactant, or a mixture thereof). Further, this detergent composition may contain other detergent components known in the art, such as builders, bleaching agents, bleaching activators, corrosion inhibitors, sequestering agents, soil-dissociating polymers, aromatics, other enzymes (e.g., protease, lipase, or amylase), enzyme stabilizers, formulation assistants, fluorescent brightening agents, foaming promoters, etc. Examples of representative anionic surfactants include linear alkyl benzene sulfonate (LAS), alkylsulfate (AS), α-olefin sulfonate (AOS), polyoxyethylene alkyl ether sulfate (AES), α-sulfonato fatty acid methyl ester (α-SFMe), and alkali metal salts of natural fatty acids. Examples of nonionic surfactants include polyoxyethylene alkyl ether (AE), alkyl polyethylene glycol ether, nonylphenol polyethylene glycol ether, fatty acid methyl ester ethoxylate, fatty acid esters of sucrose or glucose, and esters of alkyl glucoside and polyethoxylated alkylglucoside.

The use of the proteins or the cellulase preparation of the present invention in a detergent composition can improve performances regarding particulate soil removal, color clarification, fuzz prevention, depilling, and reduction of stiffness.

The present invention relates to a method of deinking waste paper using a deinking agent wherein the proteins or the cellulase preparation of the present invention is used in a step of deinking waste paper with a deinking agent.

When the protein or the cellulase preparation of the present invention is acted on waste paper, the efficiency of deinking is enhanced, and thus, the protein or the cellulase preparation of the present invention is useful in the process of manufacturing recycled paper from waste paper. This deinking method can significantly decrease ink-remaining fibers. Therefore, the whiteness of the waste paper can be enhanced.

The aforementioned "deinking agent" is not particularly limited as long as it is a commonly used agent when deinking waste paper. Examples thereof include alkali such as NaOH or $Na_2CO_3$, sodium silicate, hydrogen peroxide, phosphates, anionic surfactants, nonionic surfactants, capturing agents such as oleic acid, and examples of aids include pH stabilizers, chelating agents, and dispersants.

Waste paper, which can be treated by the above deinking method, is not particularly limited as long as it can be generally referred to as waste paper. Examples of waste paper include: used printed paper containing mechanical pulp and chemical pulp such as used newspaper, used magazine paper and low-grade or middle-grade used printed paper; used wood-free paper composed of chemical pulp; and coated paper thereof. Further, the above deinking method can be applied to any paper on which ink has been deposited if the paper is not generally referred to as waste paper.

Further, the present invention relates to a method for improving drainage of paper pulp. This method comprises a step of treating the paper pulp with the proteins or the cellulase preparation of the present invention.

According to this method, drainage of paper pulp can be remarkably improved without significant deterioration in paper strength. Pulp, which can be treated by this method, is not particularly limited, and examples thereof include waste paper pulp, recycled board pulp, kraft pulp, sulfite pulp, processed or thermo-mechanical pulp, and other high-yield pulp.

The present invention further relates to a method for improving the digestibility of animal feeds. This method comprises a step of treating animal feeds with the proteins or the cellulase preparation of the present invention.

According to this method, molecular weights of glucans in animal feeds are suitably lowered. Thus, the digestibility of animal feeds can be improved.

5. Deposition of Microorganisms

The *Rhizopus oryzae* CP96001 strain was deposited at the International Patent Organism Depositary of the National Institute of Advanced Industrial Science and Technology (Tsukuba Central 6, 1-1-1 Higashi, Tsukuba, Ibaraki, Japan) under the accession number of FERM BP-6889 on Apr. 21, 1997.

The *Mucor circinelloides* CP99001 strain was deposited at the International Patent Organism Depositary of the National Institute of Advanced Industrial Science and Technology (Tsukuba Central 6, 1-1-1 Higashi, Tsukuba, Ibaraki, Japan) under the accession number of FERM BP-6890 on Jul. 2,1999.

The *Phycomyces nitens* CP99002 strain was deposited at the International Patent Organism Depositary of the National Institute of Advanced Industrial Science and Technology (Tsukuba Central 6, 1-1-1 Higashi, Tsukuba, Ibaraki, Japan) under the accession number of FERM BP-6891 on Jul. 2, 1999.

The *Escherichia coli* JM 109 strain that was transformed with the expression vector pMKD01 used in the present invention was deposited at the International Patent Organism Depositary of the National Institute of Advanced Industrial Science and Technology (Tsukuba Central 6, 1-1-1 Higashi, Tsukuba, Ibaraki, Japan) under the accession number of FERM BP-5974 (initial deposition: FERM P-15730, date of initial deposition: Jul. 12, 1996).

The *Humicola incolens* MN 200-1 strain that can be a host for the expression vector of the present invention was deposited at the International Patent Organism Depositary of the National Institute of Advanced Industrial Science and Technology (Tsukuba Central 6, 1-1-1 Higashi, Tsukuba, Ibaraki, Japan) under the accession number of FERM BP-5977 (initial deposition: FERM P-15736, date of initial deposition: Jul. 15, 1996).

This description includes part or all of the contents as disclosed in the description of Japanese Patent Application No. 2000-354296, which is a priority document of the present application.

BEST MODES FOR CARRYING OUT THE PRESENT INVENTION

The present invention is described in more detail with reference to the following examples and reference examples but is not limited thereto.

In the following description, "endoglucanase activity" refers to CMCase activity. Further, "CMCase activity" measured by the amount of the reducing sugars released after the incubation of a cellulase enzyme and a carboxymethylcellulose (CMC, Tokyo Kasei Kogyo, Japan) solution for a given period of time and one unit is defined as the amount of an enzyme that produces reducing sugars corresponding to 1 µmol of glucose per minute.

In implementing the following tests, examples disclosed in WO 98/03667 and WO 00/24879 were referred to.

REFERENCE EXAMPLES

Reference Example 1 cDNA Cloning of Cellulase NCE5

(1) Isolation of cDNA and Preparation of Library

In the screening of the gene that encodes NCE5, the cellulase component, mRNA was prepared from *Humicola insolens* MN 200-1 (FERM BP-5977), and cDNA was synthesized by a reverse transcriptase to prepare a library.

(i) Preparation of Total RNA

*Humicola insolens* MN 200-1 (FERM BP-5977) was cultured in medium (N) (5.0% Avicel, 2.0% yeast extract, 0.1% polypeptone, 0.03% calcium chloride, 0.03% magnesium chloride, pH 6.8) for 2 days, and cells were collected by centrifugation (3,500 rpm, 10 minutes). Among the collected cells, 3 g thereof was washed with sterilized water, frozen in liquid nitrogen, and then ground in liquid nitrogen using a mortar and a pestle. Total RNA was isolated from the ground cells using ISOGEN (Nippon Gene) in accordance with the manual attached thereto, and total RNA was confirmed by formaldehyde agarose gel electrophoresis as a chromatic figure.

(ii) Preparation of Poly(A)tail+RNA (=mRNA)

Among the total RNA prepared in (i), 1 mg thereof was applied on the oligo (dT) cellulose column to elute and isolate mRNA using the mRNA Purification Kit (Amersham Pharmacia Biotech) in accordance with the attached manual. Further, mRNA was confirmed by formaldehyde agarose gel electrophoresis as a smear chromatic figure.

(iii) Synthesis of cDNA cDNA was synthesized from 5 μg of the mRNA prepared in (ii) using the Time Saver cDNA Synthesis Kit (Amersham Pharmacia Biotech) in accordance with the attached manual.

(iv) Preparation of cDNA Library

The EcoRI-NotI adaptor contained in the Time Saver cDNA Synthesis Kit was ligated to the blunt end of the synthesized total cDNA in accordance with the attached manual. The total amount of this DNA fragment was ligated into the phage vector and the EcoRI arm of the λZAPII Cloning Kit (Stratagene) using the DNA Ligation Kit Ver. 2 (Takara Shuzo Co., Ltd.), followed by ethanol precipitation. Thereafter, the DNA fragment was dissolved in a TE (10 mM Tris hydrochloride, pH 8.0, 1 mM EDTA) buffer. The thus obtained recombinant phage vector was subjected to in vitro packaging using the Gigapack m Plus Packaging Extract (Stratagene) in accordance with the attached manual. Thereafter, this recombinant phage vector was infected with *Escherichia coli* XL1-Blue MRF' and cultured on a plate for plaque formation. Thus, a phage library was obtained. With the use thereof, an object gene was cloned.

(2) Amplification and Analysis of DNA by PCR

DNA was amplified by PCR using the cDNA prepared in (1)-(iii) as a template based on the information concerning partial amino acid sequences of the cellulase NCE5.

The following synthetic oligonucleotides were prepared as primers.

```
N-terminal: 5'-TAY TGG GAY TGY TGY AAR CC-3' (20mer) (SEQ ID NO: 36)

T-43.0:     5'-TCI GCR TTI ARR AAC CAR TC-3' (20mer) (SEQ ID NO: 37)
```

(In these nucleotide sequences, R indicates G or A; Y indicates T or C; and I indicates inosine.)

PCR was carried out in 50 μg of reaction solution using 1 μof cDNA as a template, 1.25 units of LA Taq DNA Polymerase (Takara Shuzo Co., Ltd.) and its attached buffer, 0.2 mM dNTP, 10% DMSO, and 1 μM each of the above primers under the following condition: at 94° C. for 1 minute, (at 94.0° C. for 30 seconds, 55.0° C. for 30 second, and 72° C. for 1 minutes)×25 times, and 72.0° C. for 1 minute)×25 times, and 72.0° C. for 5 minutes.

About 500 bp DNA was amplified by this reaction, and the amplified DNA was subjected to sequencing using the DYEnamic ET Terminator Cycle Sequencing Premix Kit (Amersham Pharmacia Biotech) and the ABI PRISM 310 Genetic Analyzer (PE Applied Biosystems) in accordance with the attached protocols. As a result, the amino acid sequence, which was deduced from the determined nucleotide sequence, contained all the partial amino acid sequences of cellulase NCE5. Thus, the deduced amino acid sequence was used as a probe in the following screening process.

(3) Cloning of the Gene that Encodes NCE5, the Cellulase Component (i) Screening by Plaque Hybridization The 500 bp DNA fragment (100 ng) amplified by PCR was previously labeled with the ECL Direct DNA/RNA Labeling Detection System (Amersham Pharmacia Biotech).

The phage plaque prepared in (1)-(iv) was transferred to the Hybond-N+ nylon transfer membrane (Amersham Pharmacia Biotech) and subjected to alkali treatment with 0.4N sodium hydroxide. Recombinant phage DNA on the membrane was denatured into a single strand. Thereafter, the nylon membrane was washed with 5×SSC (1×SSC: 15 MM trisodium citrate, 150 mM sodium chloride) and then air dried to immobilize DNA thereon. Thereafter, the nylon membrane was hybridized in accordance with the manual of the kit, detected, and exposed to Fuji Medical X-ray film (Fuji Photo Film) to yield 6 positive clones.

(ii) Preparation of Phage DNA

DNA was prepared from the positive clones as plasmid DNA in accordance with the manual attached to the kit.

A plasmid in which a DNA fragment was cloned into pBluescript SK(−) was prepared from ampicillin-resistant *Escherichia coli* SOLR™. Using this plasmid as a template, PCR was carried out using the N-terminal and T-43.0 primers used in (2) under the same conditions as described above. As a result, a 500 bp amplification product was obtained from one plasmid. Thus, it is deduced that the object DNA was cloned into this plasmid. This plasmid was digested with EcoRI and then subjected to agarose gel electrophoresis.

As a result, the plasmid was found to contain about 1 kbp EcoRI fragment.

(4) Determination of cDNA Nucleotide Sequence

A nucleotide sequence of the about 1 kbp EcoRI fragment that was inserted into a positive recombinant pBluescript SK(−) plasmid obtained in (3)-(ii) was determined in the same manner as described above using primers for sequencing T3 and T7. As a result, this nucleotide sequence was found to contain a 672 bp open reading frame (ORF). Amino acid sequences deduced from the nucleotide sequence and the ORF were shown in SEQ ID NO: 39 and SEQ ID NO: 38 in the Sequence Listings.

Further, 1 to 18 amino acid sequences in this ORF were considered to be signal sequences for secreting the protein extracellularly.

Reference Example 2

Expression of NCE5 Gene in *Humicola insolens*

Plasmid pJD01 (see Example D1 (2) (b) in WO 00/24879) was used as an expression vector in *Humicola insolens* MN 200-1 (FERM BP-5977) and constructed in the following manner.

(1) Construction of NCE5 Expressing Plasmid pJND-c5

(i) Site-Directed Mutagenesis into NCE5 Gene

In order to ligate the NCE5 gene to the BamHI site of plasmid pJD01, a primer was constructed so as to previously comprise BamHI site in a sequence immediately upstream of the initiation codon and that immediately downstream of the termination codon, and the NCE5 gene was amplified by PCR. Primers for mutagenesis were designed as shown below.

NCE5-N-BamHI:
5'-GGGGATCCTGGGACAAGATGCAGCTCCCCCTGACCACG-3'; (38mer) (SEQ ID NO: 40)

NCE5-C-BamHI:
5'-GGGGATCCTGCATTTAACGCGAGCAGCCGCTCTTGGCC-3'. (38mer) (SEQ ID NO: 41)

PCR was carried out under the same conditions as described above using the positive recombinant pBluescript SK(−) plasmid obtained in Reference Example 1 as a template. As a result, an about 670 bp amplification product of the DNA fragment was confirmed by 1.0% agarose gel electrophoresis. Unreacted matter was removed by the MicroSpin S400 HR Columns (Amersham Pharmacia Biotech), precipitated with ethanol, and then digested with BamHI. Subsequently, a total amount was subjected to 1.0% agarose gel electrophoresis, a 670 bp DNA fragment was collected using the Sephaglas BandPrep Kit (Amersham Pharmacia Biotech) in accordance with the attached manual, and the BamHI fragment was subcloned into the BamHI site of plasmid pUC118 to yield plasmid pNCE5Bam. Further, the nucleotide sequence of this inserted fragment was determined and confirmed by the aforementioned method.

(ii) Preparation of Plasmid pJND-c5

The above plasmid pJD01 was digested with BamHI and separated by 0.8% agarose gel electrophoresis. An about 8.0 kbp DNA fragment was collected by the Sephaglas BandPrep Kit, and the collected DNA fragment was dephosphorylated using *Escherichia coli*-derived alkaline phosphatase (Takara Shuzo Co., Ltd.) in accordance with the attached manual. Similarly, the plasmid pNCE5Bam obtained in (i) was digested with BamHI, and 670 bp DNA fragments were collected and ligated to the above DNA fragment using the DNA Ligation Kit Ver. 2 to obtain expression plasmid pJND-c5.

(2) Transformation of *Humicola Incolens* with Plasmid pJND-c5

*Humicola insolens* MN 200-1 (FERM BP-5977) was cultured in medium (S) at 37° C. for 24 hours, and then the cells were collected by centrifugation at 3,000 rpm for 10 minutes. Medium (S) is composed of medium (N) described in Reference Example 1 having glucose (3.0%) added thereto and Avicel removed therefrom. The collected cells were washed with 0.5M sucrose and suspended in 10 ml of enzyme solution for preparing protoplast (3 mg/ml β-glucuronidase, 1 mg/ml Chitinase, 1 mg/ml Zymolyase, and 0.5M sucrose) filtered through a 0.45 μm filter. The suspension was shaken at 30° C. for 60 to 90 minutes to render fungal threads to be protoplasted. This suspension was filtered and then centrifuged at 2,500 rpm for 10 minutes, and the protoplast was collected and then washed with a SUTC buffer (0.5M sucrose, 10 mM calcium chloride, and 10 mM Tris hydrochloride (pH 7.5)).

The thus prepared protoplast was suspended in 1 mL of SUTC buffer, and 10 μl of DNA (TE) solution was added to the suspension in amounts of 10 μg per each 100 μl of the suspension. The mixture was allowed to stand in ice for 5 minutes. Subsequently, 400 μl of PEG solution (60% PEG 4000, 10 mM calcium chloride, 10 mM Tris hydrochloride (pH 7.5)) was added and the mixture was allowed to stand in ice for 20 minutes. Thereafter, 10 ml of SUTC buffer was added, and centrifugation was carried out at 2,500 rpm for 10 minutes. The collected protoplast was suspended in 1 ml of SUTC buffer, centrifuged at 4,000 rpm for 5 minutes, and finally suspended in 100 μl of SUTC buffer.

The protoplast treated as above was superposed on the hygromycin-added (200 μg/ml) YMG medium (1% glucose, 0.4% yeast extract, 0.2% malt extract, 1% agar (pH 6.8)) together with YMG soft agar. Culture was incubated at 37° C. for 5 days. Thereafter, the generated colony was determined to be a transformant.

EXAMPLE 1

Construction of Gene Expressing RCE I Variant H43, which Lacks the Cellulose-Binding Domain Plasmid p18-1 containing the codon optimized endoglucanase gene RCE I (see Example D3 (1) g) in WO 00/24879) was digested with the restriction enzyme BamHI to prepare plasmid pR1H4 wherein a fragment containing the codon optimized endoglucanase gene has been cloned into the BamHI site of plasmid pUC118. This plasmid pR1H4 was used as a template to perform first-phase PCR using two synthetic DNAs, i.e., RC-43F and RC-43R, as primers and the TaKaRa LA PCR in vitro Mutagenesis Kit (Takara Shuzo Co., Ltd.). Reaction conditions were in accordance with the manual attached to the kit. A sample was separated after the reaction by agarose gel electrophoresis to obtain an about 650 bp gene fragment 43-X2.

Using plasmid pJND-c5 as a template, which comprises the NCE5 gene originally having no cellulose-binding domain and being a family 45 endoglucanase as described in Reference Example 2, first-phase PCR was similarly carried out using two synthetic DNAs, i.e., NX-43F and NX-43R, as primers and the TaKaRa LA PCR in vitro Mutagenesis Kit (Takara Shuzo Co., Ltd.). Reaction conditions were in accordance with the manual attached to the kit. A sample was separated after the reaction by agarose gel electrophoresis to obtain an about 120 bp gene fragment 43-X1.

RC-43F:   CACCACGCGCTACTGGGACT;   (SEQ ID NO: 20)
RC-43R:   GGATCCTGCGTTTACTTGC;    (SEQ ID NO: 21)
NX-43F:   GGATCCTGGGACAAGATG;     (SEQ ID NO: 22)
NX-43R:   GCACGACGGCTTGCAGC       (SEQ ID NO: 23)

Annealing and second-phase PCR were carried out using PCR fragments 43-X1 and 43-X2 and the TaKaRa LA PCR in vitro Mutagenesis Kit. Two synthetic DNAs, i.e., NX-43F and RC-43R, were used as primers and reaction conditions were in accordance with the manual attached to the kit. A sample was separated after the reaction by agarose gel electrophoresis to obtain an about 700 bp gene fragment H43. This fragment was digested with the restriction enzyme BamHI to prepare plasmid pR1H43 ligated to the BamHI site of plasmid pUC118 using the TaKaRa DNA Ligation Kit Ver. 1. Reaction conditions, such as those regarding enzymes, were in accordance with the manual attached to the kit. The obtained plasmid pR1H43 was subjected to sequencing using the Cy5-Auto Read Sequencing Kit (Amersham Pharmacia), and the sequence was analyzed using the DNA Sequencer ALFred (Amersham Pharmacia). A primer used in the reaction was the M13 primer, which was attached to the kit. As a result, it was confirmed that the sequence was in the expected form, i.e., a secretion signal on the N-terminal side was derived from NCE5 and the remaining catalytic active domain (CAD) was a sequence derived from RCE I. The amino acid sequence of the RCE I variant H43 deduced from the nucleotide sequence is shown below.

H43: MQLPLTTLLTLLPALAAAQSGSGRTTRYWDCCKPSCSWPGKANVSSPVKSCNKDG(SEQ ID NO: 24)

VTALSDSNAQSGCNGGNSYMCNDNQPWAVNDNLAYGFAAAAISGGGESRWCCSCFELTF

TSTSVAGKKMVVQVTNTGGDLGSSTGAHFDLQMPGGGVGIFNGCSSQWGAPNDGWGSR

YGGISSASDCSSLPSALQAGCKWRFNWFKNADNPSMTYKEVTCPKEITAKTGCSRK

In this amino acid sequence (SEQ ID NO: 24), amino acid residues 1 to 18 are signal peptides derived from NCE5, amino acid residues 19 to 24 are N-terminal sequences of NCE5, amino acid residues 25 to 36 are sequences derived from NCE5 or RCE I, and amino acid residue 37 and succeeding sequences are derived from the catalytic active domain of RCE I.

When the reaction is carried out in accordance with the above method, two types of sequences, i.e., the sequence as shown in SEQ ID NO: 24 and the sequence in which amino acid residue 34 is alanine, are obtained as amino acid sequences of the protein coded by the nucleotide sequence of the gene fragment H43. In the following procedure, a gene fragment used has a nucleotide sequence, which encodes the amino acid sequence as shown in SEQ ID NO: 24.

EXAMPLE 2

Construction of Gene Expressing RCE I Variant H45, which Lacks the Cellulose-Binding Domain pR1H4 obtained in Example 1 was used as a template to introduce amino acid substitution into the RCE I gene using synthetic DNA, RC-A121P, and the TaKaRa LA PCR in vitro Mutagenesis Kit (Takara Shuzo Co., Ltd.). Reaction conditions were in accordance with the manual attached to the kit. A sample was separated after the reaction by agarose gel electrophoresis to obtain an about 1 kbp gene fragment L9. This fragment was digested with the restriction enzyme BamHI and ligated to the BamHI site of plasmid pUC118 using the TaKaRa DNA Ligation Kit Ver. 1 to prepare plasmid pR1L9. Reaction conditions, such as those regarding enzymes, were in accordance with the manual attached to the kit. The obtained plasmid pR1L9 was subjected to sequencing reaction using the Cy5-Auto Read Sequencing Kit (Amersham Pharmacia), and the sequence was analyzed using the DNA Sequencer ALFred (Amersham Pharmacia). A synthetic DNA used as primer in this reaction was H4-RI. As a result, it was confirmed that the sequence was in the expected form, i.e., one alanine was substituted with proline.

RC-A121P: GACTGCTGCAAGCCGTCGTGC; (SEQ ID NO: 42)

H4-R1:    GTTGCACATGTAGGAGTTGC   (SEQ ID NO: 43)

Using this pR1L9 as a template, a gene encoding a portion of the secretion signal sequence in the RCE I gene was amplified. PCR was carried out using two synthetic DNAs, i.e., RC-451F and RC451R, as primers, the TaKaRa Ex Taq Polymerase (Takara Shuzo Co., Ltd.), and attached buffers. The composition of the reaction solution was in accordance with the conditions specified in the attached manual. The temperature conditions for the Thermal Cycler (2400-R, Perkin Elmer) were 25 cycles of 94° C. for 1 minute, 50° C. for 2 minutes, and 72° C. for 1 minute. A sample was separated after the reaction by agarose gel electrophoresis to obtain an about 100 bp gene fragment 45-X1.

Similarly, a region encoding the catalytic active domain (CAD) of the RCE I gene was amplified using the pR1L9 as a template. PCR was carried out using two synthetic DNAs, i.e., RC-452F and RC-452R, as primers, the TaKaRa Ex Taq Polymerase (Takara Shuzo Co., Ltd.), and attached buffers. The composition of the reaction solution was in accordance with the conditions specified in the attached manual. The temperature conditions for the Thermal Cycler (2400-R, Perkin Elmer) were 25 cycles of 94° C. for 1 minute, 50° C. for 2 minutes, and 72° C. for 1 sample was separated after the reaction by agarose gel electrophoresis to obtain an about 630 bp gene fragment 45-X2.

RC-451F: GCGGATCCTGGGACAAGATG;      (SEQ ID NO: 25)

RC-451R: GCCTGCAGAGCGGCGGAGGCCATC;  (SEQ ID NO: 26)

RC-452F: GCCTGCAGGGAAAGTACAGCGCTGT; (SEQ ID NO: 27)

RC-452R: GCGGATCCTGCGTTTACTTGC      (SEQ ID NO: 28)

PCR fragments 45-X1 and 45-X2 were digested with the restriction enzyme PstI, ligated together using the TaKaRa DNA Ligation Kit Ver. 1, and then digested with the restriction enzyme BamHI to obtain a DNA fragment 45-X3. PCR was carried out using 45-X3 as a template, two synthetic DNAs, i.e., RC-451F and RC-452R, as primers, the TaKaRa Ex Taq Polymerase (Takara Shuzo Co., Ltd.), and attached buffers. The composition of the reaction solution was in accordance with the conditions specified in the attached manual. The temperature conditions for the Thermal Cycler (2400-R, Perkin Elmer) were 25 cycles of 94° C. for 1 minute, 50° C. for 2 minutes, and 72° C. for 1 minute. A sample was separated after the reaction by agarose gel electrophoresis to obtain an about 700 bp gene fragment H45. This fragment was digested with the restriction enzyme BamhI and ligated to the BamHI site of plasmid pUC 118 using the TaKaRa DNA Ligation Kit Ver. 1 to prepare plasmid pR1H45. Reaction conditions were in accordance with the manual attached to the kit. The amino acid sequence of the RCE I variant H45 deduced from the nucleotide sequence is shown below.

```
H45: MKFITIASSALLALALGTEMASAALQGKYSAVSGGASGNGVTTRYWDCCKPSCSW(SEQ ID NO: 29)

PGKANVSSPVKSCNKDGVTALSDSNAQSGCNGGNSYMCNDNQPWAVNDNLAYGFAAA

AISGGGESRWCCSCFELTFTSTSVAGKKMVVQVTNTGGDLGSSTGAHFDLQMPGGGVGIF

NGCSSQWGAPNDGWGSRYGGISSASDCSSLPSALQAGCKWRFNWFKNADNPSMTYKEV

TCPKEITAKTGCSRK
```

In this amino acid sequence (SEQ ID NO: 29), amino acid residues 1 to 23 are signal peptides derived from RCE1, amino acid residue 24 is an N-terminal sequence of RCE I, amino acid residues 25 and 26 are sequences introduced by a primer used, and amino acid residue 27 and succeeding sequences are derived from the catalytic active domain of RCE I.

EXAMPLE 3

Expression of Codon Optimized Endoglucanase RCE I Gene and its Variants RCE I-H43 and H45, which Lack the Cellulose-Binding Domains, in *Humicola Insolens*

Plasmid pJD01 (see Example D1 (2) (b) in WO 00/24879) was digested with BamHI and dephosphorylated using *Escherichia coli*-derived alkaline phosphatase (Takara Shuzo Co., Ltd.) in accordance with the attached manual. Plasmids pR1H43 and pR1H45 obtained in Examples 1 and 2 respectively were also digested with BamHI to produce about 700 bp DNA fragments. The obtained fragments were ligated respectively with aforementioned plasmid pJD01 using the DNA Ligation Kit Ver. 1 to produce expression plasmids pJND-H43 and pJND-H45.

*Humicola insolens* MN 200-1 (FERM BP-5977) was transformed with pJND-H43, pJND-H45, or pJI4D01 comprising the codon optimized RCE I gene (plasmid comprising a codon optimized RCE I gene to express the *Rhizopus*-derived RCE I in *Humicola*, see Example D3 (3) in WO 00/24879). Specifically, *Humicola insolens* MN 200-1 (FERM BP-5977) was cultured in medium (S) (3.0% glucose, 2.0% yeast extract, 0.1% polypeptone, 0.03% calcium chloride, 0.03% magnesium chloride (pH 6.8)) at 37° C. for 24 hours, and then the cells were collected by centrifugation at 3,000 rpm for 10 minutes. The collected cells were washed with 0.5M sucrose and suspended in 10 ml of enzyme solution for preparing protoplast (5 mg/ml Novozyme 234 (Novo), 5 mg/ml Cellulase Onozuka R-10 (Yakult), and 0.5M sucrose) filtered through a 0.45 µm filter. The suspension was shaken at 30° C. for 60 to 90 minutes to render fungal threads to be protoplasted. This suspension was filtered and then centrifuged at 2,500 rpm for 10 minutes, and protoplast was collected and washed with a SUTC buffer (0.5M sucrose, 10 mM calcium chloride, and 10 mM Tris hydrochloride (pH 7.5)).

The thus prepared protoplast was suspended in 1 mL of SUTC buffer, and 10 µl of DNA (TE) solution was added to the suspension in amounts of 10 µg per each 100 µl of the suspension. The mixture was allowed to stand in ice for 5 minutes. Subsequently, 400 µl of PEG solution (60% PEG 4000, 10 mM calcium chloride, and 10 mM Tris hydrochloride (pH 7.5)) was added and the mixture was allowed to stand in ice for 20 minutes. Thereafter, 10 ml of SUTC buffer was added, and centrifugation was carried out at 2,500 rpm for 10 minutes. The collected protoplast was suspended in 1 ml of SUTC buffer, centrifuged at 4,000 rpm for 5 minutes, and finally suspended in 100 µl of SUTC buffer.

The protoplast treated as above was superposed on a 200 µg/ml hygromycin B-containing YMG medium (1% glucose, 0.4% yeast extract, 0.2% malt extract, 1% agar (pH 6.8)) together with YMG soft agar. Culture was incubated at 37° C. for 5 days. Thereafter, the generated colony was determined to be a transformant.

The obtained transformant was cultured in medium (N) (5.0% Avicel, 2.0% yeast extract, 0.1% polypeptone, 0.03% calcium chloride, 0.03% magnesium chloride, pH 6.8) at 37° C. A culture supernatant from which solid matter has been removed by centrifugation was determined to be an enzyme sample.

EXAMPLE 4

Isolation and Purification of RCE I Variant from *Humicola insolens* Transformant

*Humicola insolens* transformants were inoculated to medium (N) (5.0% Avicel, 2.0% yeast extract, 0.1% polypeptone, 0.03% calcium chloride, 0.03% magnesium chloride, (pH 6.8)) and subjected to shake culture at 37° C. Transformants into which plasmids pJND-H43 and pJND-H45 had been introduced were cultured for 5 to 6 days. Regarding transformants into which plasmid pJI4D01 had been introduced, a sample was cultured for 4 days for obtaining an RCE I enzyme, which was not degraded in its linker domain, and which sustained a cellulose-binding domain. In contrast, a sample was cultured longer than 4 days, i.e., for 5 to 6 days, for obtaining the RCE I enzyme, which was degraded in its linker domain and lacked the cellulose-binding domain. Each of the resulting culture solutions was centrifuged at 7,000 rpm for 20 minutes to remove cells, and the culture supernatant was determined to be a crude cellulase preparation.

An ammonium sulfate solution at a final concentration of 1.5 M was prepared from 100 ml of this crude cellulase preparation and then applied at a flow rate of 10.0 ml/min to Macro-Prep Methyl HIC Support hydrophobic chromatography (270 ml in gel volume, BioRad Laboratories) which had been previously equilibrated with 1.5 M ammonium sulfate solution. It was then fractionated by eluting at a flow rate of 10.0 ml/min in a stepwise elution method in which the concentration of ammonium sulfate was decreased by 0.3 M each from 1.5 M. Fractions found to have strong activity of removing fuzz from lyocell were: a fraction obtained at an ammonium sulfate concentration of 1.2 M regarding a culture solution of the transformant into which plasmid pJND-H43 had been introduced (hereinafter referred to as an "H43 culture solution"); a fraction obtained at an ammonium sulfate concentration of 0.9 M regarding a culture solution of the transformant into which plasmid pJND-H45 had been introduced (hereinafter referred to as an "H45 culture solution"); a fraction obtained at an ammonium sulfate concentration of 0.6 M regarding a culture solution of the transformant into which plasmid pJI4D01 had been introduced and cultured for 4 days (hereinafter referred to as an "H4 culture solution"); and a fraction obtained at an ammonium sulfate concentration of 0.9 M regarding a culture solution of the transformant into which plasmid pJI4D01 had been introduced and for which a culture period had been extended to accelerate its degradation (hereinafter referred to as an "H4 degradation product"). Therefore, 100 ml each of these fractions was fractionated.

An ammonium sulfate solution at a final concentration of 1.5 M was prepared from 100 ml of the obtained active fractions and then applied again at a flow rate of 10.0 ml/min to Macro-Prep Methyl HIC Support hydrophobic chromatography (270 ml in gel volume, BioRad Laboratories) which had been previously equilibrated with 1.5 M ammonium sulfate solution. It was then fractionated by eluting at a flow rate of 10.0 ml/min in a stepwise elution method in which the concentration of ammonium sulfate in deionized water was decreased by 0.15 M each from 1.5 M. Fractions found to have activities of removing fuzz from lyocell were: a fraction obtained at an ammonium sulfate concentration of 1.35 M regarding the H43 culture solution; a fraction obtained at an ammonium sulfate concentration of 1.05 M regarding the H45 culture solution; a fraction obtained at an ammonium sulfate concentration of 0.75 M regarding the H4 culture solution; and a fraction obtained at an ammonium sulfate concentration of 1.05 M regarding the H4 degradation product. Therefore, 40 ml each of these fractions was fractionated.

An ammonium sulfate solution at a final concentration of 1.5 M was prepared from 40 ml of the obtained active fractions and then applied at a flow rate of 4.0 ml/min to Macro-Prep Methyl HIC Support hydrophobic chromatography (25 ml in gel volume, BioRad Laboratories) which had been previously equilibrated with 1.5 M ammonium sulfate solution. It was then fractionated by eluting at a flow rate of 4.0 ml/min in deionized water. Among these fractions, 8 ml of fraction, which was found to have strong activity of removing fuzz from lyocell, was fractionated.

Acetate buffer (150 ml, 50 mM, pH 4.0) was prepared by diluting the obtained active fractions, and the resulting buffer was then applied at a flow rate of 2 ml/min to MonoS 10-/10-HR column (Amersham Pharmacia), which had been previously equilibrated with 50 mM acetate buffer (pH 4.0). It was then fractionated by eluting at a flow rate of 2 ml/min in a stepwise elution method in which the concentration of NaCl in 50 mM acetate buffer (pH 4.0) was increased by 0.1 M each to 1M NaCl in 50 mM acetate buffer (pH 5.0). Fractions that were obtained at a NaCl concentration of about 0.2 to 0.3M were found to have activity of removing fuzz from lyocell. Therefore, 6 ml of fraction found to have the strongest activity was fractionated. These fractions showed in SDS-PAGE a single band of about 25 KDa regarding proteins purified from the H43 culture solution, the H45 culture solution, and the H4 degradation product and a single band of about 40 KDa regarding the protein purified from the H4 culture solution.

SDS-PAGE was carried out using the system of Tefco in which an electrophoresis tank (No. 03-101), a source (Model: 3540), 10% gel (01-015), and a buffer kit for SDS-PAGE (06-0301) were used. The condition for electrophoresis was 18 mA/10 min and then 20 mA/90 min. In protein detection after the electrophoresis, silver staining was carried out using a 2D-silver staining reagent II "DAIICHI" (Daiichi Pure Chemicals Co., Ltd.) for electrophoresis. A standard protein used as a marker was the SDS-PAGE molecular weight standard protein, Low Range (161-0304, BioRad).

The activity of removing fuzz from lyocell was measured in accordance with the following method.

Color knitted fabric of lyocell (Toyoshima Japan) was fuzzed in a large washer together with a surfactant and rubber balls. Thereafter, the fuzzy knitted fabric of lyocell (Toyoshima Japan, 9 cm×10 cm, about 2 g in weight) was cylindrically sewn and subjected to fuzz removal treatment with various enzymes under the conditions as set forth below. The protein concentrations required to completely remove fuzz existing in the cylindrical fabric by this treatment were calculated.

The protein concentrations of various endoglucanases were calculated from the peak area at UV 280 nm of respective endoglucanase eluted with a linear gradient from 0% to 80% of acetonitrile concentration in 0.05% TFA (trifluoroacetic acid) at a flow rate of 1.0 ml/min in HPLC analysis using TSK gel TMS-250 column (4.6 mm I.D.×7.5 cm, TOSOH Japan). The standard used was the purified NCE4, which was analyzed in HPLC under the same conditions, the protein concentration of which had been preliminarily measured by the protein assay kit (BioRad Laboratories). The standard used to measure the protein concentration for the protein assay kit was albumin standard (Bovine serum albumin, fraction V, PIERCE). The purified NCE4 (coded by nucleotides 118 to 1088 in SEQ ID NO: 18) was isolated and purified from a culture solution of *Humicola insolens* according to the method described in WO 98/03640.

Test machine: Launder Meter L-12 (Daiei Kagaku Seiki MFG, Japan)

Temperature: 55° C.

Time: 60 minutes

Reaction volume: 40 ml

Reaction pH: pH 5 (10 mM acetate buffer)

pH 6 (10 mM acetate buffer)

The treating liquid contained 4 rubber balls (about 16 g each) together with the endoglucanase solution.

EXAMPLE 5

Identification of N-Terminal Amino Acid Sequences of RCE I Variant Protein Isolated and Purified from *Humicola insolens* Transformant In order to determine the N-terminal amino acid sequences of the purified proteins obtained in Example 4, each of the fractions was subjected to SDS-PAGEmini (Tefco), electroblotted on a PVDF membrane, stained with Coomassie Brilliant Blue R-250 (Nacalai Tesque, Inc.), decolorized, washed with water, and then air dried. A portion on which the object protein had been blotted was cleaved out therefrom and subjected to a Protein Sequencer (Model 492, PE Applied Biosystems) to analyze the N-terminal amino acid sequence. The amino acid sequences were read from enzymes that were purified from the H45 culture solution, the H4 culture solution, and the H4 degradation product without any problem. Regarding the enzyme purified from the H43 culture solution, however, no signal was generated by Edman degradation and the N-terminal amino acid was found to be modified and protected. Thus, this enzyme was immersed in a solution of 0.5% polyvinyl pyrrolidone (molecular weight: 40,000, Sigma)/100 mM acetic acid at 37° C. for 30 minutes, and, after a protein unbound portion on the membrane was blocked, this enzyme was treated with Pfu Pyroglutamate Aminopeptidase (Takara Shuzo Co., Ltd.) at 50° C. for 5 hours to remove the modified N-terminal residue. Thus, sequencing was carried out once more. The obtained sequences were as shown below.

```
The N-terminal amino acid sequence of RCE I-H43:
Gln-Ser-Gly-Ser-Gly-Arg-Thr.      (SEQ ID NO: 30)
(7 residues)

The N-terminal amino acid sequence of RCE I-H45:
Lys-Tyr-Ser-Ala-Val-Ser-Gly; and  (SEQ ID NO: 31)
(7 residues)

Ala-Val-Ser-Gly-Gly-Ala-Ser.      (SEQ ID NO: 32)
(7 residues)

The N-terminal amino acid sequence of RCE I-H4
(25KDa):
Ser-Ala-Val-Ser-Gly-Gly-Ala; and  (SEQ ID NO: 33)
(7 residues)

Gly-Gly-Ala-Ser-Gly-Asn-Gly.      (SEQ ID NO: 34)
(7 residues)

The N-terminal amino acid sequence of RCE I-H4
(40KDa):
Ala-Glu-(Cys)-Ser-Lys-Leu-Tyr.    (SEQ ID NO: 35)
(7 residues)
```

As a result of identification of N-terminal amino acid sequences, it was found that only the enzyme purified from the H4 culture solution (hereinafter referred to as "RCE I-H4 (40 KDa)") had a cellulose-binding domain (CBD) while any of the remaining enzyme purified from the H43 culture solution (hereinafter referred to as "RCE I-H43 (25 KDa)"), the enzyme purified from the H45 culture solution (hereinafter referred to as "RCE I-H45 (25 KDa)"), or the enzyme purified from the H4 degradation product (hereinafter referred to as "RCE I-H4 (25 KDa)") had no cellulose-binding domain (CBD) but had only the catalytic active domains (CAD).

EXAMPLE 6

Comparison of Specific Activity of Removing Fuzz from Cotton Fabric between RCE I which Lacks the Cellulose-Binding Domain, and RCE I, which has the Cellulose-Binding Domain Using the endoglucanase which was homogenously purified in Example 5, a knitted cotton fabric (a 6 cm×8 cm fabric from cotton smooth knit No. 3900, Nitto Boseki Co., Ltd., dyed in brown by reactive dye at Tsuyatomo Senko), which has been fuzzed in a large washer, was subjected to fuzz removal under the following conditions. The amount of fuzz remaining unremoved was visually evaluated, and the amount of purified enzyme to be added so that the amount of remaining fuzz would reach 50% was determined. The amount of protein was determined using the BCA Protein Assay Reagent PIERCE) in accordance with the conditions described in the attached manual. The estimated molecular weight of the 40 KDa purified RCE I protein (RCE I-H4 (40 KDa)) is about 1.5 times higher than those of the 25 KDa purified RCE I proteins (RCE I-H43 (25 KDa)), RCE I-H45 (25 KDa)), and RCE I-H4 (25 KDa)). Accordingly, even though the quantified amounts of proteins are the same, the number of enzyme molecules in the 40 KDa purified RCE I protein is only about two-thirds of that in the 25 KDa purified RCE I protein in terms of the number of enzyme molecules contained in the protein.

Test machine: Launder Meter L-20 (Daiei Kagaku Seiki MFG, Japan)
Temperature: 40° C. or 55° C.
Time: 120 minutes
Reaction volume: 40 ml
Reaction pH: Reacted at pH 7 (1 mM phosphate buffer, prepared using deionized water).
The treating liquid contained 4 rubber balls (about 16 g each) together with the enzyme solution.
The results are as shown in Table 2 below.

TABLE 2

|  | The amount of enzyme added 40° C. | The amount of enzyme added 55° C. |
|---|---|---|
| Purified RCE I-H4 (40 KDa) | 390 μg or more | 390 μg or more |
| Purified RCE I-H4 (25 KDa) | 18 μg | 53 μg |

As is apparent from the results shown in Table 2, the 25 KDa protein, which lacks the cellulose-binding domain (CBD), exhibits much higher activity of removing fuzz from cotton fabrics than the 40 KDa protein, which has the cellulose-binding domain (CBD), even though both proteins are originated from the same *Zygomycetes*-derived endoglucanases RCE I.

EXAMPLE 7

Comparison of Specific Activity of Removing Fuzz from Lyocell Fabric between RCE I which Lacks the Cellulose-Binding Domain, and RCE I, which has the Cellulose-Binding Domain Using the endoglucanase which was homogenously purified in Example 5, a lyocell fabric (6 cm×8 cm, Toyoshima Japan) was subjected to fuzz removal under conditions improved from the method described in Example 4. The amount of fuzz remaining unremoved was visually evaluated, and the amount of purified enzyme required to completely remove fuzz was determined. The amount of protein was determined using the BCA Protein Assay Reagent (PIERCE) in accordance with the conditions described in the attached manual. The estimated molecular weight of the 40 KDa purified RCE I protein (RCE I-H4 (40 KDa)) is about 1.5 times higher than those of the 25 KDa purified RCE I proteins (RCE I-H43 (25 KDa)), RCE I-H45 (25 KDa)), and RCE I-H4 (25 KDa)). Accordingly, even though the quantified amounts of proteins are the same, the number of enzyme molecules in the 40 KDa purified RCE I protein is only about two-thirds of that in the 25 KDa purified RCE I protein in terms of the number of enzyme molecules contained in the protein.

Test machine: Launder Meter L-20 (Daiei Kagaku Seiki MFG, Japan)
Temperature: 40° C.
Time: 90 minutes
Reaction volume: 50 ml
Reaction pH: Reacted at pH 6 (10 mM acetate buffer, prepared using deionized water).
The treating liquid contained 4 rubber balls (about 16 g each) together with the enzyme solution.
The results are as shown in Table 3 below.

TABLE 3

|  | The amount of enzyme added |
|---|---|
| Purified RCE I-H4 (40 KDa) | 32 μg |
| Purified RCE I-H4 (25 KDa) | 11 μg |

As is apparent from the results shown in Table 3, RCE I, which is *Zygomycetes*-derived endoglucanase, exhibits a higher specific activity of removing fuzz from lyocell fabrics as the 25 KDa protein, which lacks the cellulose-binding domain (CBD), than as the 40 KDa protein, which has the cellulose-binding domain (CBD).

EXAMPLE 8

Comparison of Specific Activity of Removing Fuzz from Cotton Fabric between RCE I which Lacks the Cellulose-Binding Domain, and RCE I which has the Cellulose-Binding Domain, Under Alkaline, Low-Temperature, and Surfactant-Present Conditions Using the endoglucanase which was homogenously purified in Example 5, a knitted cotton fabric (a 6 cm×8 cm fabric from cotton smooth knit No. 3900, Nitto Boseki Co., Ltd., dyed in brown by reactive dye at Tsuyatomo Senko), which had been fuzzed in a large washer, was subjected to fuzz removal under the following conditions. The amount of fuzz remaining unremoved was visually evaluated, and the amount of purified enzyme to be added so that the amount of remaining fuzz would reach 50% was determined. The amount of protein was determined using the BCA Protein Assay Reagent (PIERCE) in accordance with the conditions described in the attached manual. The estimated molecular weight of the 40 KDa purified RCE I protein (RCE I-H4 (40 KDa)) is about 1.5 times higher than those of the 25 KDa purified RCE I proteins (RCE I-H43 (25 KDa)), RCE I-H45 (25 KDa)), and RCE I-H4 (25 KDa)). Accordingly, even though the quantified amounts of proteins are the same, the number of enzyme molecules in the 40 KDa purified RCE I protein is only about two-thirds of that in the 25 KDa purified RCE I protein in terms of the number of enzyme molecules contained in the protein.

Test machine: Launder Meter L-20 (Daiei Kagaku Seiki MFG, Japan)

Temperature: 30° C.

Time: 120 minutes

Reaction volume: 40 ml

Reaction pH: Reacted at pH 10 (5 mM sodium carbonate buffer, prepared using deionized water).

The treating liquid contained a nonionic surfactant Persoft NK-100 (NOF Corp.) at a final concentration of 100 ppm together with the enzyme solution and 4 rubber balls (about 16 g each).

The results are as shown in Table 4 below.

TABLE 4

|  | The amount of enzyme added |
|---|---|
| Purified RCE I-H4 (40 KDa) | 390 μg or more |
| Purified RCE I-H4 (25 KDa) | 52 μg |

As is apparent from the results shown in Table 4, given the low-temperature, alkaline, and surfactant-present conditions under which detergents are actually used, the 25 KDa protein, which lacks the cellulose-binding domain (CBD), exhibits much higher activity of removing fuzz from cotton fabrics than the 40 KDa protein, which has the cellulose-binding domain (CBD), even though both proteins are originated from the same *Zygomycetes*-derived endoglucanases RCE I.

EXAMPLE 9

Comparison of Specific Activity of Removing Fuzz from Cotton Fabric among Various Purified RCE I Proteins which Lack the Cellulose-Binding Domains Using the endoglucanase which was homogenously purified in Example 5, a knitted cotton fabric (a 6 cm×8 cm fabric from cotton smooth knit No. 3900, Nitto Boseki Co., Ltd., dyed in brown by reactive dye at Tsuyatomo Senko), which had been fuzzed in a large washer, was subjected to fuzz removal under the following conditions. The amount of fuzz remaining unremoved was visually evaluated, and the amount of purified enzyme to be added so that the amount of remaining fuzz would reach 50% was determined. The amount of protein was determined using the BCA Protein Assay Reagent (PIERCE) in accordance with the conditions described in the attached manual. The estimated molecular weight of the 40 KDa purified RCE I protein (RCE I-H4 (40 KDa)) is about 1.5 times higher than those of the 25 KDa purified RCE I proteins (RCE I-H43 (25 KDa)), RCE I-H45 (25 KDa)), and RCE I-H4 (25 KDa)). Accordingly, even though the quantified amounts of proteins are the same, the number of enzyme molecules in the 40 KDa purified RCE I protein is only about two-thirds of that in the 25 KDa purified RCE I protein in terms of the number of enzyme molecules contained in the protein.

Test machine: Launder Meter L-20 (Daiei Kagaku Seiki MFG, Japan)

Temperature: 40° C.

Time: 120 minutes

Reaction volume: 40 ml

Reaction pH: Reacted at pH 7 (1 mM phosphate buffer, prepared using deionized water).

The treating liquid contained 4 rubber balls (about 16 g each) together with the enzyme solution.

The results are as shown in Table 5 below.

TABLE 5

|  | The amount of enzyme added |
|---|---|
| Purified RCE I-H4 (40 KDa) | 390 μg or more |
| Purified RCE I-H43 (25 KDa) | 26 μg |
| Purified RCE I-H45 (25 KDa) | 18 μg |
| Purified RCE I-H4 (25 KDa) | 18 μg |

As is apparent from the results shown in Table 5, various RCE I proteins such as RCE I-H43 (25 KDa), RCE I-H-45 (25 KDa), and RCE I-H4 (25 KDa), which lack the cellulose-binding domains, exhibit much higher activity of removing fuzz from cotton fabrics than the 40 KDa protein RCE I-H4 (40 KDa), which has the cellulose-binding domain (CBD). This indicates that the RCE I protein, which lacks the cellulose-binding domain (CBD), exhibits much higher activity of removing fuzz from cotton fabrics than the 40 KDa protein, which has the cellulose-binding domain (CBD), regardless the length of the linker domain remaining on the N-terminal side of the catalytic active domain. Also, whether or not it is an artificial or non-artificial deficiency, the RCE I protein, which lacks the cellulose-binding domain (CBD), exhibits much higher activity of removing fuzz from cotton fabrics than the 40 KDa protein RCE I-H4 (40 KDa), which has the cellulose-binding domain (CBD).

EXAMPLE 10

Comparison of Specific Activity of Removing Fuzz from Lyocell Fabric among Various Purified RCE I Proteins, which Lack the Cellulose-Binding Domains Using the endoglucanase which was homogenously purified in Example 5, a lyocell fabric (6 cm×8 cm, Toyoshima Japan) was subjected to fuzz removal under conditions improved from the method described in Example 4. The amount of fuzz remaining unremoved was visually evaluated, and the amount of purified enzyme required to completely remove fuzz was determined. The amount of protein was determined using the BCA Protein Assay Reagent (PIERCE) in accordance with the conditions described in the attached manual. The estimated molecular weight of the 40 KDa purified RCE I protein (RCE I-H4 (40 KDa)) is about 1.5 times higher than those of the 25 KDa purified RCE I proteins (RCE I-H43 (25 KDa)), RCE I-H45 (25 KDa)), and RCE I-H4 (25 KDa)). Accordingly, even though the quantified amounts of proteins are the same, the number of enzyme molecules in the 40 KDa purified RCE I protein is only about two-thirds of that in the 25 KDa purified RCE I protein in terms of the number of enzyme molecules contained in the protein.

Test machine: Launder Meter L-20 (Daiei Kagaku Seiki MFG, Japan)
Temperature: 40° C.
Time: 90 minutes
Reaction volume: 40 ml
Reaction pH: Reacted at pH 6 (10 mM acetate buffer, prepared using deionized water).

The treating liquid contained 4 rubber balls (about 16 g each) together with the enzyme solution.

The results are as shown in Table 6 below.

TABLE 6

|  | The amount of enzyme added |
| --- | --- |
| Purified RCE I-H4 (40 KDa) | 32 µg |
| Purified RCE I-H43 (25 KDa) | 12 µg |
| Purified RCE I-H45 (25 KDa) | 11 µg |
| Purified RCE I-H4 (25 KDa) | 11 µg |

As is apparent from the results shown in Table 6, various RCE I proteins such as RCE I-H43 (25 KDa), RCE I-H45 (25 KDa), and RCE I-H4 (25 KDa), which lack the cellulose-binding domains, exhibit higher activity of removing fuzz from lyocell fabrics than the 40 KDa protein RCE I-H4 (40 KDa), which has the cellulose-binding domain (CBD). This indicates that the RCE I protein, which lacks the cellulose-binding domain (CBD), exhibits higher activity of removing fuzz from lyocell fabrics than the 40 KDa protein, which has the cellulose-binding domain (CBD) regardless the length of the linker domain remaining on the N-terminal side of the catalytic active domain. Also, whether or not it is an artificial or non-artificial deficiency, the RCE I protein, which lacks the cellulose-binding domain (CBD), exhibits higher activity of removing fuzz from lyocell fabrics than the 40 KDa protein RCE I-H4 (40 KDa), which has the cellulose-binding domain (CBD).

All publications, patents, and patent applications cited herein are incorporated herein by reference in their entirety.

INDUSTRIAL APPLICABILITY

When Zygomycetes-derived endoglucanase such as RCE I, RCE II, RCE III, MCE I, MCE II, or PCE I, which lacks the cellulose-binding domain, is allowed to act, the endoglucanase activity can be significantly enhanced in comparison with endoglucanase having a cellulose-binding domain. Accordingly, fabric treatment such as reduction of fuzzing, improvement in feel and appearance, color clarification, partial color change, and softening of cellulose-containing fabrics and improvement in deinking of waste paper and drainage of paper pulp can be effected with a smaller amount of enzymes. This can decrease necessary costs remarkably.

Free Text of Sequence Listings
SEQ ID NO: 13: codon optimized sequence corresponding to RCE I protein (SEQ ID NO: 2)
SEQ ID NO: 17: consensus amino acid sequence found in the cellulose-binding domain of family 45 endoglucanase
SEQ ID NO: 20 to 23: primers
SEQ ID NO: 24: recombinant protein
SEQ ID NO: 25 to 28: primers
SEQ ID NO: 29: recombinant protein
SEQ ID NO: 30 to 35: N-terminal amino acid sequence of recombinant protein
SEQ ID NO: 36 and 37: primers
SEQ ID NO: 38: NCE5 amino acid sequence
SEQ ID NO: 39: NCE5 cDNA sequence
SEQ ID NO: 40 to 43: primers

---

The invention claimed is:

1. An isolated protein comprising the amino acid sequence of SEQ ID NO: 1 except for amino acids 3 to 38 that include the cellulose-binding domain and which protein exhibits endoglucanase activity.

2. An isolated protein consisting essentially of the amino acid sequence of SEQ ID NO: 1 except for amino acids 3 to 38 that include the cellulose-binding domain and which protein exhibits endoglucanase activity.

3. An isolated polynucleotide encoding the protein according to claim 1.

4. An expression vector comprising the polynucleotide according to claim 3.

5. An isolated host cell transformed with the expression vector according to claim 4.

6. The host cell according to claim 5, which is a filamentous fungus.

7. The host cell according to claim 6, which is a microorganism belonging to *Humicola*.

8. A method for producing a protein comprising the amino acid sequence of SEQ ID NO: 1 except for amino acids 3 to 38 that include the cellulose-binding domain and which protein exhibits endoglucanase activity, wherein said method comprises the steps of culturing the host cell according to claim 5 and collecting the protein produced by culturing said host cell.

9. An isolated protein produced by the method according to claim 8.

10. A cellulase preparation comprising the protein according to claim 1.

11. A method for reducing the rate at which cellulose-containing fabrics become fuzzy or reducing fuzz in cellulose-containing fabrics comprising the step of bringing cellulose-containing fabrics into contact with the protein according to claim 1.

12. A method of weight loss treatment of cellulose-containing fabrics to improve the feel and appearance of said cellulose-containing fabrics comprising the step of bringing cellulose-containing fabrics into contact with the protein according to claim 1.

13. A method of color clarification of colored cellulose-containing fabrics comprising the step of contacting the colored cellulose-containing fabrics with the protein according to claim 1.

14. A method of providing colored cellulose-containing fabrics with partial color change comprising the step of contacting the colored cellulose-containing fabrics with the protein according to claim 1.

15. A method for reducing the rate at which cellulose-containing fabrics become stiff or reducing stiffness in cellulose-containing fabrics comprising the step of contacting the cellulose-containing fabrics with the protein according to claim 1.

16. A detergent additive comprising the protein according to claim 1 in a non-dusting granular form or a stabilized liquid form.

17. A detergent composition comprising the protein according to claim 1.

18. A method of deinking waste paper wherein said method comprises the step of contacting waste paper with a deinking agent and the protein according to claim 1.

19. A method for improving drainage of paper pulp comprising the step of contacting paper pulp with the protein according to claim 1.

20. A method for improving digestibility of animal feeds comprising the step of adding the protein of claim 1 to animal feeds.

21. An isolated protein which exhibits endoglucanase activity, the protein being selected from the group consisting of:
   (a) the protein having the amino acid sequence of SEQ ID NO: 1 except for the amino acids 3-38, and
   (b) a protein comprising an amino acid sequence having 95% or more sequence identity to the protein of (a).

22. The protein according to claim 21 having the amino acid sequence of SEQ ID NO: 24.

23. The protein according to claim 21 having the amino acid sequence of SEQ ID NO: 29.

24. The protein according to claim 21 comprising the amino acid sequences of SEQ ID NO: 33 and SEQ ID NO: 34.

* * * * *